United States Patent [19]
Khwaja et al.

[11] Patent Number: 6,113,907
[45] Date of Patent: *Sep. 5, 2000

[54] PHARMACEUTICAL GRADE ST. JOHN'S WORT

[75] Inventors: Tasneem A. Khwaja, Corona Del Mar; Elliot P. Friedman, Montecito, both of Calif.

[73] Assignees: University of Southern California, Los Angeles; Pharmaprint Inc., Irvine, both of Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/956,602

[22] Filed: Oct. 23, 1997

Related U.S. Application Data

[63] Continuation-in-part of application No. 08/838,198, Apr. 15, 1997, abandoned.

[51] Int. Cl.$^7$ .................................................... A61K 35/78

[52] U.S. Cl. ......................................................... 424/195.1

[58] Field of Search ........................................ 424/195.1

[56] References Cited

U.S. PATENT DOCUMENTS

| | | | |
|---|---|---|---|
| 5,401,502 | 3/1995 | Wunderlich et al. | 424/195.1 |
| 5,716,928 | 2/1998 | Benet et al. | 514/11 |
| 5,780,037 | 7/1998 | Khwaja | 424/195.1 |
| 5,798,101 | 8/1998 | Haveson | 424/195.1 |
| 5,849,734 | 12/1998 | Tehim et al. | 514/217 |

FOREIGN PATENT DOCUMENTS

| | | |
|---|---|---|
| 0 599 307 A1 | 11/1993 | European Pat. Off. . |
| 0 702 957 A1 | 9/1994 | European Pat. Off. . |
| 39 35 772 | 4/1991 | Germany . |
| WO 96/32122 | 10/1996 | WIPO . |
| WP 97/13489 | 4/1997 | WIPO . |

OTHER PUBLICATIONS

Georgiev E. Nauchn Tr Plovoiv 32(1)257–63, 1985.

Baureithel K. Inhibition of Benzodiazepine Binding in vitro by Amentoflavone, A Constituent of Various Species of Hypericum. Pharmaceutica Acta Helvetiae 72(3)153–157, Mar. 1997.

Stephenson F. Purification and Characterization of the Brain GABA/Benzodiazepine Receptor. Structural and Functional Properties, Alan R. Liss, Inc. 261–274, 1986.

Scholfield P. Sequence and Functional Expression of the GABA Receptor Shows a Ligand Gated Receptor Super Family. Nature 328 221–227, Jul. 1987.

Chatterjee S. Hyperforin as a Possible Antidepressant Component of Hypericum Extracts. Life Sciences 63(6)499–510, 1998.

Denke A. Biochemical Activites of Extracts from *Hypericum perforatum* L. Arzneim Forsch/Drug Res 49(2)109–114, 1999.

Cott. J. In Vitro Receptor Binding and Enzyme Inhibition by *Hypericum perforatum* Extract. Pharmacopsychiatry 30(Supplement 2)108–112, 1997.

Muller W. In Vitro Study of Hypericum Extract, Hypericine and Camphor Oil as Antidepressants. Deutsche Apotherker Zeitung 136(13)1015–1022, Mar. 1996.

English translation of Georgiev E.

English translation of Chatterjee, EP 0 599 307.

Colegate S. Bioactive Natural Products. CRC Press, Boca Raton FL, pp. 3, 200–201, 1993.

Steinback R. Problems in Purifying and Standardizing a Phytopharmaceutical, For Example Hypericum. J of Applied Phytotherapy vol. 6, pp. 221–224, English translation provided, 1981.

Liao J. Evaluation with Receptor Binding Assay on the Water Extracts of Ten CNS Active Chinese Herbal Drugs. Proc National Science. 19(3)151–158, 1995.

Rossi, G. Biological Testing, Chapter 31. Remington's Pharmaceutical Sciences, Phila College of Pharmacy and Science 16th Ed, 1980.

Khwaja T. Recent Studies on the Anticancer Activities of Mistletoe and Its Alkaloids. Oncology 43(Sup 1)42–50, 1986.

Dingermann T., Phytopharmaceuticals in Old Age, Pharmazeutische Zeitung 140(23)9–14, 16, Jun. 1995.

Rocha L., An Antifungal Pyrone and Xanthones with Monoamine Oxodase Inhibitory Activity from *Hypericum Brasiliense* 36(6)1381–1385, Jun. 1994.

Nissen, H., Quality Control of Phytopharaca with HPLC, GIT Fachz Lab 31(4)293–5, Apr. 1987.

Seabra R., Analysis of Commerically Available Hypericum Extracts, Rev Port Farm 41(3)39–42, Mar. 1992.

Han G., The Screening of Chinese Traditional Drugs by Biological Assay and the Isolation of Some Active Components, Int J of Chinese Medicine 16(1)1–17, Mar. 1991.

Killmer L., How LC/MS Can Help Solve Your Pharmaceutical Analysis Problems, Today's Chemist at Work, Feb. 1996.

Muller et al., "Johanniskraut—In–vitro–Studie uber Hypericum–Extract, Hypericin und Kampferol als Antidepressiva", Deutsche Apotheker Zeitung (136 Jahrgang), No. 13, pp. 17–24 (1015–1022), Mar. 28, 1996. (English translation also provided.)

Raffa, "Screen of Receptor and Uptake–Site Activity of Hypericin Component of St. John's Wort Reveals σ Receptor Binding", Life Sciences, vol. 62, No. 16, pp. PL 265–270, 1998.

*Primary Examiner*—Ralph Gitomer
*Attorney, Agent, or Firm*—Lyon & Lyon LLP

[57] ABSTRACT

The present invention relates generally to St. John's Wort materials and methods for making such materials in medicinally useful and pharmaceutically acceptable forms. More particularly, the present invention relates to the use of compositional and activity fingerprints in the processing of St. John's Wort materials to produce drugs which qualify as pharmaceutical grade compositions which are suitable for use in clinical or veterinary settings to treat and/or ameliorate diseases, disorders or conditions.

2 Claims, 6 Drawing Sheets

PHARMACEUTICAL GRADE ST. JOHN'S WORT

This is a continuation-in-part of U.S. Ser. No. 08/838,198, filed on Apr. 15, 1997 now abandoned.

TABLE OF CONTENTS
1. FIELD OF THE INVENTION
2. BACKGROUND OF THE INVENTION
2.1 ST. JOHN'S WORT
2.2 CLINICAL STUDIES OF ST. JOHN'S WORT
2.2.1 MILD-TO-MODERATE DEPRESSION
   Animal Studies
2.2.2 ANTIVIRAL ACTIVITY
2.2.3 WOUND-HEALING EFFECTS
2.2.4 MISCELLANEOUS EFFECTS
3. SUMMARY OF THE INVENTION
3.1. DEFINITIONS
4. BRIEF DESCRIPTION OF THE DRAWINGS
5. DETAILED DESCRIPTION OF THE INVENTION
5.1. METHODS OF PHARMAPRINTING®
5.1.1. METHODS OF DEVELOPING A PHARMAPRINT®
5.1.2. ALTERNATIVE METHODS OF DEVELOPING A PHARMAPRINT®
5.1.3 ADDITIONAL VARIATIONS ON THE METHOD OF DEVELOPING A PHARMAPRINT®
5.2. METHODS OF PROCESSING AND EXTRACTING BOTANICAL MATERIALS
5.2.1 LIQUID EXTRACTS OF PLANT MATERIALS AND POWDERED PLANT MATERIALS
5.3 SEPARATION OF FRACTIONS
5.4 ESTABLISHMENT OF APPROPRIATE BIOASSAYS
5.4.1. ENZYMATIC AND RECEPTOR BASED ASSAYS
5.4.2 CELL CULTURE AND OTHER ASSAYS
5.4.3. ANTICANCER ACTIVITY
5.4.4. ANTIVIRAL ACTIVITY
5.5. ANALYTICAL METHODS FOR ANALYZING CHEMICAL COMPONENTS
5.6. ANALYSIS OF FRACTIONS
5.7. METHODS OF USE OF PHARMAPRINTED® MATERIALS
5.8. PHARMPRINT® OF ST. JOHN'S WORT
5.8.1. BIOLOGICAL PHARMAPRINT®
5.8.2. CHEMICAL COMPONENTS
5.8.3. CONVERSION RATIO
6. EXAMPLE: ST. JOHN'S Wort, *Hypericum perforatum*
6.1 COMMERCIAL SUPPLIERS/PRODUCT NAMES
6.2 FRACTIONAL ANALYSIS ON A SILICA GEL COLUMN
6.3 BIOLOGICAL ACTIVITY ANALYSIS MONOAMINE OXIDASE, SEROTONIN TRANSPORTER ASSAY, OTHER ASSAYS
6.3.1 BIOASSAY FOR $GABA_A$ BINDING
6.3.2 BIOASSAY FOR NMDA AGONIST SITE BINDING
6.3.3 BIOASSAY FOR $M_1$ BINDING
6.3.4 MONOAMINE OXIDASE-A ($MAO_A$)
6.3.5 MONOAMINE OXIDASE B
6.3.6 SEROTONIN TRANSPORTER ASSAY
6.3.7 SUMMARY OF BIOASSAYS
6.4 ACTIVE COMPONENTS OF ST. JOHN'S WORT IN THE LITERATURE
6.4.1 ST. JOHN'S WORT COMPONENTS
6.4.2 HYPERICIN CONTENT OF ST. JOHN'S WORT
6.4.3 FLAVONOID CONTENT OF ST. JOHN'S WORT
6.4.4 ESSENTIAL OIL FROM ST. JOHN'S WORT
6.4.5 PHLOROGLUCINOLS IN ST. JOHN'S WORT
6.4.6 MISCELLANEOUS COMPOUNDS IN ST. JOHN'S WORT
6.4.7 ANALYTICAL METHODS OF ANALYSIS
6.4.8 THIN LAYER CHROMATOGRAPHY (TLC) OF HYPERICIN AND PSEUDOHYPERICIN
   Sample Preparation
   Standard Preparation
   Stability of Standards/Sample Solutions
   Stop Test
   Chromatographic Conditions
6.4.9 HIGH PERFORMANCE LIQUID CHROMATOGRAPHY (HPLC) OF HYPERICIN AND PSEUDOHYPERICIN
   Limits of Quantitation and Detection
   HPLC (Flavonoids, Hypericin and Pseudohypericin) Extraction
6.4.10 UV/VIS SPECTROSCOPIC METHOD (HYPERICIN/PSEUDOHYPERICIN) SAMPLE PREPARATION
6.5 HPLC ANALYSIS OF ST. JOHN'S WORT COMPONENTS HYPEROSIDE, RUTIN, QUERCETIN, QUERCITRIN, HYPERICIN, MANGIFERIN
6.6 CONTRIBUTION OF COMPONENTS TO TOTAL ACTIVITY OF ST. JOHN'S WORT

1. FIELD OF THE INVENTION

The present invention relates generally to botanical materials and methods for transforming such materials into medicinally useful and pharmaceutically acceptable forms. More particularly, the present invention relates to the use of compositional and activity fingerprints in the processing of St. John's Wort to produce botanical drugs which qualify as pharmaceutical grade compositions which are suitable for use in clinical settings to treat and/or ameliorate diseases, disorders and/or conditions.

2. BACKGROUND OF THE INVENTION

Pharmaceutical manufacturing is based on control over the composition and bioactivity for each manufactured batch. This standardization and control provides reproducible material in the predictable and consistent treatment of patients. Herbal medicines, produced from botanical materials, have presented a unique problem for manufacturers desiring the control, reproducibility, and standardization that are required of pharmaceuticals. This problem is primarily due to the plurality of components contained in an herbal medicine and the large variation in composition and potency due to the growing, harvesting and processing conditions of raw materials.

Plants have been, and continue to be, the source of a wide variety of medicinal compounds. For centuries, various forms of botanically derived materials have been used to treat countless different ailments. The botanical materials have typically been in the form of powders made from one or more plants or plant parts or extracts derived from whole plants or selected plant parts. These powders and extracts are, for the most part, complex mixtures of both biologically active and biologically inactive compounds.

Although plant powders and extracts have been used widely for medicinal purposes, there are a number of problems associated with the use of such medicaments. For example, the complex chemical nature of the botanical materials makes it difficult to use the botanical materials in any type of controlled and predictable manner. The potential variations in the chemical composition of different batches of material obtained from different plant harvests makes such materials unsuitable for use in clinical situations.

On a positive note, the complex groupings of bioactive components typically found in botanical materials presents the potential for synergistic or additive bioactivity profiles. However, these potential increases in medicinal effectiveness are not predictable due to the unknown nature of these complex materials.

The above problems associated with the inherent chemical complexity of botanical medicaments has resulted in a great deal of effort being directed to the separation and isolation of the biologically active components from numerous medicinally important botanical materials. This area of endeavor has expanded rapidly in conjunction with the many improvements in chemical separation and analysis technology. Once isolated and purified, the various active components are used in clinical settings to establish the medicinal effectiveness of a specific component. Separation and purification of individual components from botanical materials is the cornerstone of this type of drug development procedure. Once purified, the suspected active component is typically mixed with a pharmaceutically acceptable carrier and subjected to further studies in laboratory animals and eventual clinical trials in humans. Upon proof of clinical efficacy, these types of drugs are considered to be pharmaceutical grade because they contain a single, or at most a small number of, well-characterized compounds which are present in known quantities.

Pharmaceutical grade drugs are advantageous in that they allow careful tracking of the effects of individual compounds in treatment protocols. Further, the dosage of the drug can be carefully controlled to provide relatively predictable medicinal action. A disadvantage of the relative purity of such pharmaceutical grade drugs is that the potential for complex and synergistic biological activity provided by naturally occurring plant materials is reduced because of the isolation of the drug from its natural environment. The study of isolated products may also represent artifacts produced by breakdown of sensitive biological/botanical complexes. The potential benefit provided by such synergistic activity is believed by many industry experts to be outweighed by the clinical risks associated with the use of complex plant materials which are not well characterized or controlled in a clinical setting.

Although isolation and purification of single compounds from plant materials has been a popular form of drug research and development, there has also been interest in studying complex botanical extracts to characterize their medicinal qualities. Many complex plant materials and extracts exist which have potent, but relatively unpredictable, medicinal properties. These materials are, for the most part, useless in a clinical setting because of the inherent risks involved with treating patients with poorly characterized materials which have no established batch consistency and which may differ widely in composition. Accordingly, there is a need to provide methods for standardizing such complex botanical materials so that they may be used more effectively in clinical research and patient treatments.

2.1 ST. JOHN'S WORT

There are many sources and many forms of St. John's Wort. It may be derived from the stem, leaf, flowers, buds. The herb, or portions thereof, may also be in the form of a freeze dried powdered extract. An oil extract of the crushed flowers may be prepared. Various forms of infusions (aqueous), oil macerates, or alcohol water extractions are available.

2.2 CLINICAL STUDIES OF ST. JOHN'S WORT

By way of background and introduction, this section summarizes information to-date regarding clinical indications for which St. John's Wort is useful. St. John's Wort has been the subject of many clinical studies on the extract and the botanical itself. The major clinical indication is the alleviation of mild to moderate depression. Other clinical indications include AIDS, antibacterial uses, anticancer uses, antimutagenic uses, antiviral uses, use as an immunostimulant and use for immunosuppression.

2.2.1 MILD-TO-MODERATE DEPRESSION

St. John's Wort has become increasingly popular in Germany where physicians routinely prescribe herbal medicines. In 1994, 66 million daily doses of St. John's Wort were prescribed there for use in the treatment of depression (De Smet and Nolen, 1996, *British Medical Journal* 313:241–247). This phytomedicine has now been tested in more than 3,000 patients against placebo and various active medications (Hänsgen et al., 1994, *Nervenheilkunde* 12:285–289; Harrer et al., 1994, *J. Geriatric Psychiatry Neurology* 7:S24–28; Hübner et al., 1994, *J. Geriatric Psychiatry Neurology* 7:S12–14; Martinez et al., 1994, *J. Geriatric Psychiatry Neurology* 7:S29–33; Sommer and Harrer, 1994, *J. Geriatric Psychiatry Neurology* 7:S9–11; Vorbach et al., 1994, *J. Geriatric Psychiatry Neurology* 7:S19–23; Woelk et al., 1994, *J. Geriatric Psychiatry Neurology* 7:S34–38). The primary formulations used in the German clinical trials are summarized in the Table below. All these formulations are standardized according to total content of hypericin-like compounds (including pseudohypercin) as assessed by a spectrophotometric assay.

TABLE

St. John's Wort Preparations (Depression Studies)

| Preparation name | Total Extract/day | Total Hypericin/day |
|---|---|---|
| Jarsin ™ (tablets) | 900 mg | 1 mg |
| Jarsin ™ 300 (tablets) | 900 mg | 2.7 mg |
| Psychotonin ™ (drops) | 350–500 mg | 0.5–0.75 mg |
| Neuroplant ™ (caps) | 500 mg | 1 mg |
| Hyperforat ™ | N/A | 0.4–0.6 mg |
| Sedariston ™* | 300–600 mg | 0.45–0.9 mg |

*Also contains valerian extract

German researchers (with a colleague from San Antonio, Tex.) recently published a meta-analysis of 23 randomized trials of St. John's Wort with a total of 1,757 outpatients with mild to moderately severe depressive disorders. They concluded that the herb was significantly superior to placebo, and appeared comparably effective to standard antidepressants while producing fewer side effects (Linde, 1996, *British Medical Journal* 313:253–258).

The controlled studies of St. John's Wort's efficacy in depression included in the meta-analysis were randomized, or "quasi-randomized" through alternation. Comparisons were made of the herb alone, or in combination with other plant extracts, to placebo and/or a standard antidepressant. Twenty of the 23 trials were double-blind, one was single blind, and two were open label. Most were 4 to 8 weeks in duration. The methodological quality of each study was assessed by at least two reviewers to determine eligibility for inclusion in the meta-analysis.

In each study, improvement in depressive symptoms had been evaluated with depression scales most commonly the Hamilton depression scale (HAM-D) and the clinical global impressions index (CGI). The daily dose of either hypericin, the reference substance for standardization, or of total extract varied considerably between studies, from 0.4, 2.7 mg and 300 and 1000 mg.

In 13 studies comparing a single St. John's Wort preparation with placebo, 55.1 percent (225) of patients receiving the herb were improved, compared with 22.3 percent (94) responding to the placebo. In the comparisons to standard antidepressants, in three trials with single preparations and two with combinations, 63.9 percent (101) of patients responded to single preparations compared with 58.5 percent (93) with standard antidepressants, and 67.7 percent (88) responded to combination extract products (St. John's Wort and Valeriana) compared with 50 percent (66) with standard antidepressants.

The researchers acknowledged the problems in drawing valid conclusions from the pooled data of quite heterogeneous studies. These problems are compounded by the different amounts and preparations of the herb used across the studies and the possibility that hypericin is not the only bioactive component.

These limitations aside, Linde and colleagues find sufficient evidence to conclude that St. John's Wort is better than placebo in treating some depressive disorders. These data were inadequate, however, to judge whether it is as effective as standard antidepressants, although it appears to cause fewer side effects. They consider that these initial indications of efficacy warrant the undertaking of longer controlled trials comparing several doses of different St. John's Wort preparations to standard antidepressants. In separate commentary accompanying the meta-analysis, Netherlands researchers Peter De Smet and Willen Nolen agreed that these data are promising, but not yet sufficient to accept St. John's Wort as an effective antidepressant preparation (De Smet and Nolen, 1996, *British Medical Journal* 313:241–247). Besides the need for dose standardization and adequate trial lengths, they call for studies in severely depressed patients and long-term studies to assess the risk of relapse and emergence of late side effects (De Smet and Nolen, supra).

In another single blind study of patients with Seasonal Affective Disorder (DSM-III-R criteria) it was observed that 900 mg of St. John's Wort daily was equal to the effects of conventional light therapy (Kapser et al., 1996, 2nd International Congress on Phytomedicine, Munich).

Animal Studies

A commercial standardized extract of St. John's Wort (Psychotonin™) was tested in several animal models predictive of psychotropic activity (Okpanyi and Weicher, 1987, *Arzneim-Forsch* 37:10–13). These activities included two used for antidepressants: increased activity in a water wheel test in mice, and reduced aggressiveness in isolated male mice. In a recent presentation, Butterweck et al., compared the St. John's Wort extract, LI 160, with bupropion, a synthetic antidepressant (Butterweck et al. 2nd International Congress on Phytomedicine. Munich; 1996). The authors found that both drugs resulted in similar effects including the tail suspension test (mice) and the forced swim test (rats). Since St. John's Wort treatment was antagonized by drugs known to reduce dopamine functional activity (haloperidol, sulpiride, $\chi$-methyltyrosine, and $\gamma$-butyrolactone), the authors concluded that St. John's Wort exerts its activity via dopaminergic activation.

A hepatoprotective activity of a water/alcohol extract has been reported in mice at a dose of 500 mg/kg intraperitoneally. This conclusion was based on the ability of St. John's Wort to increase bile duct flow in rats and to reduce $CCl_4$-induced narcosis in barbiturate treated mice. Müller et al., (1996) reported that the St. John's Wort extract, LI 160, resulted in a 15% down-regulation of $\beta$-adrenergic receptors in the rat frontal cortex after subchronic treatment (250 mg/kg for 2 weeks). In the same study, these authors found a 25% down-regulation after similar doses (10 times the clinical dose) of imipramine.

IN VITRO STUDIES

While previous studies report that hypericin inhibits MAO at concentrations of 50 $\mu$g/ml (e.g., Suzuki et al., 1984, *Planta Medica*. 50:272–274), others have failed to confirm this effect (Bladt and Wagner, 1994, *J. Geriatric Psychiatry Neurology* 7:S57–59; Demisch et al., 1989, *Pharmacopsychiatry* 22:194; Thiede and Walper, 1994, *J. Geriatric Psychiatry Neurology* 7:S54–56). One explanation is that the hypericin used by Suzuki was apparently an extract of only 80% purity. It is possible that one or more constituents of the remaining 20% of this preparation could account for this weak enzyme inhibition. This possibility is supported by Bladt and Wagner (1994) which shows that the St. John's Wort fractions with the greatest MAO inhibition contain the highest concentration of flavonoids. Computer modeling of St. John's Wort constituents also suggests flavonoids to be the most likely MAO inhibitor fraction (H öltje and Walper, 1993, *Nervenheilkunde* 12:339–340); and in a related species (*Hypericum brasiliense*) the xanthone fraction was most active, particularly against $MAO_A$ (Rocha et al., 1994, *Phytochemistry* 36).

However, the MAO inhibition shown for St. John's Wort may not be pharmacologically relevant, since it could not be confirmed in vivo. Bladt and Wagner (1994) reported that no MAO inhibition was seen ex vivo after administration of 300 mg/kg St. John's Wort extract to rats. Whether this is due to a rapid metabolism of the active constituents or to other reasons cannot be said with certainty at this point. However, pharmacokinetic studies with the St. John's Wort extract, LI 160, showed plasma levels of only 1.5 ng/ml of hypericin after a single 300 mg dose and 8.5 ng/ml at steady state in human volunteers (Staffeldt et al., 1994, *J. Geriatric Psychiatry Neurology* 7:S47–53). Unless the active compounds are present in much larger quantities than hypericin, or are concentrated in synaptic terminals, these blood levels are several orders of magnitude below the concentrations needed to inhibit MAO. Inhibition of another degradative catecholamine enzyme, catechol-o-methyltransferase (COMT), can also be seen with various ethanolic St. John's Wort fractions at supra-physiologic concentrations of up to 500 $\mu$g/ml (Thiede and Walper, 1994). Other proposed mechanisms involve effects on serotonin. Müller and Rossel (1994) report that St. John's Wort extract inhibits serotonin receptor expression at 50 $\mu$M (~25 $\mu$g/ml (according to the way these authors use the term "molarity" when referring to a crude extract) and Perovic and Müller (1995) reported inhibition of serotonin uptake ($IC_{50}$=6.2 $\mu$g/ml) (Müller and Rossel, 1994, *J. Geriatric Psychiatry Neurology* 7:S63–64; Perovic and Müller, 1995, *Arzneim-Forsch* 45:1145–1148). The concentration required for the former effect could surely never be achieved in the whole animal and even the latter concentration seems unlikely. As a reference comparison, M üller et al. reported an $IC_{50}$ for the synthetic antidepressant, clomipramine, of 0.9 nM (~0.3 ng/ml) for serotonin uptake inhibition (Müller et al., 1996, 2nd International Congress on Phytomedicine, Munich; 1996). In addition, Müller et al. also reported an inhibition of both synaptosomal GABA uptake ($IC_{50}$=1 μg/ml LI 160) and $GABA_A$-receptor binding ($IC_{50}$=3 μg/ml).

Another novel proposal is that St. John's Wort extract (concentration not provided) reduces cytokine expression [interleukin-6] (Thiele et al., 1994, *J. Geriatric Psychiatry Neurology* 7(suppl. 1):S60–62). The hypothesis is that interleukins can reduce depression in susceptible individuals (Smith, 1991, *Med. Hypotheses* 35:298–306). The field of psychoneuroimmunology examines the links between depression and the immune system (ref) is perhaps too new to give a definitive answer regarding this mechanism in the near future, but the link between depression and the immune system is still drawing attention (Kook, et al., 1995, *Biol. Psychiatry* 37:817–819).

2.2.2 ANTIVIRAL ACTIVITY

Hypericin is currently in early clinical trials in the U.S. as an antiviral Meruelo et al., 1988). Studies have shown that two of St. John's Wort's primary components, hypericin and pseudohypericin, inhibit a variety of encapsulated viruses, including herpes simplex (Weber et al., 1994) and the human immunodeficiency virus type 1 (HIV-1) virus associated with AIDS (Meruelo et al., 1988, PNAS 85:5230–5234). While the latter researchers have concluded that hypericin and pseudohypericin display a unique and uncommonly effective antiviral activity, Weber et al., (1994) suggest that it may be due to nonspecific association with cellular and viral membranes. Activity has also been reported against murine cytomegalovirus, Sindbis virus, (Hudson et al, 1991; Lopez-Bazzocchi et al., 1991) and equine infectious anemia virus (Carpenter and Kraus, 1991).

The antiviral activity appears to involve a photoactivation process (Kraus et al., 1990) which forms singlet oxygen and inactivates viral fusion and syncytia formation. While hypericin does show antiviral activity in vivo (mice) these photodynamic properties may limit the potential usefulness as an antiretroviral agent (Stevenson and Lenard, 1993). However, besides singlet oxygen production, hypericin can is also inhibited by hypericin. These latter effects have been linked to both the antiviral and antineoplastic activities (Lavie et al., 1995).

2.2.3 WOUND-HEALING EFFECTS

St. John's Wort has historically been one of the most relied upon botanicals for the treatment of wounds. Part of this activity is due to St. John's Wort's anti-microbial activity which is attributed to the essential oil. Flavonoids, the phloroglucinol derivatives hyperforin and adhyperforin, and the xanthone kielcorin are also considered to contribute to St. John's Wort's wound-healing effects. The essential oil and the water soluble fraction of an alcoholic extract exhibit minor antifungal and significant antibacterial activity. The tannins and flavonoids inactivated *E. coli*. At dilutions of 1:400 or 1:200 Hyperforin and adhyperforin have been reported to possess an antibiotic effect greater than that of sulfonilamide.

A burn ointment prepared by extracting 5 g of fresh flowers with 100 g of olive oil for 10 days at 20° C. was used in the treatment of $1^{st}$, $2^{nd}$ and $3^{rd}$ degree burns. First degree burns healed in 48 hours. Second and third degree burns healed without scarring $\geq$3 times as rapidly as burns treated with conventional methods. Keloid formation was inhibited. A commercial preparation (Novoimamine; containing 0.412% quercetin) was found to be effective against *Staphyloccus aureus* infection. In this regard, its effects have similarly been reported to be greater than conventional treatment with sulfonilamide.

A homeopathic tincture (1:10) of St. John's Wort was studied for its wound-healing properties, and compared with *Calendula officinalis*, another widely used wound-healing herb. The effect of orally administered tincture of St. John's Wort was more pronounced than topical application of Calendula tincture in the healing of incision, excision and dead space wounds as evidenced by an increase in epithelization, and wound breaking strength. (See the Table below).

TABLE

Tinctures of St. John's Wort and Calendula on Wound-Healing

| Wound model Parameters studies | Breaking strength (g) | Incision Epithelization period (days) | Excision % wound contraction by day | | | Dead space Granulom (mg) |
|---|---|---|---|---|---|---|
| | | | 5 | 10 | 15 | |
| Controls | 270.0 ± 22.1 | 23.00 ± 1.0* | 50.0 ± 2.1 | 70.0 ± 1.2 | 90.0 ± 0.4 | 57.0 ± 4.50 |
| St. John's Wort | 396.0 ± 18.5 | 15.00 ± 0.3* | 45.0 ± 1.2 | 88.0 ± 1.0 | 95.0 ± 1.0 | 55.3 ± 3.20 |
| Calendula (topical) | 354.0 ± 13.5 | 16.50 ± 1.0* | 40.0 ± 2.1 | 74.0 ± 0.8 | 99.0 ± 0.5 | |

$n = 7_1$
*$P < 0.001$ (Gurumadhva et al., 1991)

photo reduce oxygen to superoxide radicals and can form semiquinone radicals in the absence of light. These latter authors speculate that this ability to form semiquinones might account for the antiviral activity in the whole animals and they have maintained (since the early 1980's) the clinical utility of hypericin. Hypericin has been reported to inhibit the growth of glioma cells in tissue culture. There appears to be a photoactivation involved in its antineoplastic effect as well. Hypericin and pseudohypericin have been found to inhibit the important regulatory enzyme, protein kinase C ($IC_{50}$ of 1.7 μg/ml and 15 μg/ml, respectively). Receptor tyrosine kinase activity of epidermal growth factor

2.2.4 MISCELLANEOUS EFFECTS

St. John's Wort has been reported to be useful in a number of additional conditions. In one study the procyanidin fraction of St. John's Wort was tested in an isolated Guinea pig heart preparation and found to enhance coronary flow in the same way as the procyanidins from Crataegus (Hawthorn). The same researchers tested the procyanidin fractions in porcine isolated coronary arteries. All procyanidin fractions antagonized histamine or prostaglandin F2 alpha-induced arterial contractions (Melzer, et al., 1991). In another study, preliminary findings suggest that St. John's Wort may be useful in the treatment of chronic tension headaches.

3. SUMMARY OF THE INVENTION

This invention provides a method for making a pharmaceutical grade of botanical drug, for example St. John's Wort. The method is the process of PharmaPrinting™. In one embodiment, the method comprises the steps of: providing a botanical material of St. John's Wort which comprises a plurality of components which have a given biological activity; removing a representative aliquot from the botanical material; separating the aliquot into a plurality of marker fractions wherein each of the marker fractions comprises at least one of the active components; determining the degree of the given biological activity for each of the marker fractions to provide a bioactivity fingerprint of the aliquot; and comparing the bioactivity fingerprint of the aliquot to a bioactivity fingerprint standard which has been established for a pharmaceutical grade St. John's Wort to provide a bioactivity fingerprint comparison to determine whether the botanical material is a pharmaceutical grade St. John's Wort based on the bioactivity fingerprint comparison.

This invention also provides a method comprising the steps of: providing a botanical material of St. John's Wort which has a given biological activity, said botanical material comprising a plurality of components; separating a representative aliquot of the botanical material into a plurality of marker fractions wherein at least one of the marker fractions comprises at least one active component; determining the degree of the given biological activity for each of the marker fractions to provide a bioactivity fingerprint of the representative aliquot; and comparing the bioactivity fingerprint of the representative aliquot to a bioactivity fingerprint standard which has been established for a pharmaceutical grade St. John's Wort to determine whether the botanical material is a pharmaceutical grade St. John's Wort.

In one embodiment, one or more of the marker fractions contain one active component.

The method may also comprise the additional steps of: determining the amount of the active components in each of the marker fractions to provide a quantitative compositional fingerprint of the aliquot and comparing both the quantitative compositional and bioactivity fingerprints with a quantitative compositional and bioactivity fingerprint standard to determine whether the botanical material is a pharmaceutical grade St. John's Wort. The method may also comprise the additional steps of: determining a total bioactivity of the aliquot of the botanical material and comparing the total bioactivity of the aliquot with that of a total bioactivity of a standard which has been established for a pharmaceutical grade St. John's Wort.

The invention also provides a method for making a pharmaceutical grade St. John's Wort, the method comprising the steps of: providing a botanical material of St. John's Wort which comprises a plurality of components which have a given biological activity and wherein each active component has a standardized bioactivity profile; removing a representative aliquot from the botanical material; separating the aliquot into a plurality of marker fractions wherein each of the marker fractions comprises at least one of the active components; measuring the amount of each of the active component(s) present in each of the marker fractions; calculating the bioactivity of each of the marker fractions based on the amount of each active component present and the standardized component bioactivity profile to provide a calculated bioactivity fingerprint of the aliquot; comparing the calculated bioactivity fingerprint of the aliquot to a bioactivity fingerprint standard which has been established for a pharmaceutical grade St. John's Wort to provide a bioactivity fingerprint comparison to determine whether the botanical material is a pharmaceutical grade St. John's Wort is obtained based on the bioactivity fingerprint comparison.

In these methods, the aliquot may be separated into both biologically active and inactive components. Furthermore, the marker fractions may comprise a class of related components.

The method of the invention is useful to make a pharmaceutical grade botanical material, e.g., St. John's Wort from an appropriate botanical material which has a given or desired biological activity. Preferably, the botanical material is an extract made from plant material such as an aqueous or organic extract such as an alcoholic extract or a supercritical carbon dioxide extract or organic solvent extract which may be subject to further processing. Alternatively, the botanical material is a powdered plant material, a seed oil, an essential oil or the product of steam distillation. In one embodiment, the botanical material is a homogeneous material in a single physical state, e.g. an oil or a solution.

The botanical material may be a material derived solely from St. John's Wort. In an alternative embodiment, St. John's Wort may be combined with one or more botanical materials selected from: aloe, Asian ginseng, astragalus, bilberry, black cohosh, burdock, chamomile, chestnut, coriolus versicolor, couchgrass, crampbark, dandelion root, dong quai, echinacea, elecampane, evening primrose, eyebright, false unicorn root, feverfew, garlic, ginger, ginkgo, goldenseal, gota kola, grape seed extract, green tea, guggulipid, hawthorn, hops, ivy, kava, licorice, milk thistle, mistletoes (American, Asian and European varieties), motherwort, oats, osha, passion flower, pumpkin, pygeum, red clover, rosemary, Siberian ginseng, sarsaparilla, saw palmetto, skullcap, St. John's wort, stinging nettle, valerian, wild indigo, wild yam, and yerba mansa. The methods of the present invention for making pharmaceutical drugs encompass methods for PharmaPrinting™ St. John's Wort plus one or more of the botanicals listed above as well as pharmaceutical grade drugs containing St. John's Wort and one or more of the botanicals listed above. In one embodiment, St. John's Wort may be combined with dong quai, false unicorn root, motherwort, and/or wild yam.

By way of illustrative example, but not by way of limitation, pharmaceutical grade St. John's Wort may be combined with a pharmaceutical grade botanical material such as *V. agnus-castus,* valerian, kava, skullcap or echinacea. For *V. agnus-castus,* see U.S. patent application Ser. No. 08/955,410, entitled "PHARMACEUTICAL GRADE VITEX AGNUS CASTUS", filed concurrently, incorporated in its entirety by reference herein. For valerian, see U.S. patent application Ser. No. 08/956,615, entitled "PHARMACEUTICAL GRADE VALERIAN", filed concurrently, incorporated in its entirety by reference herein. For kava, see U.S. patent application Ser. No. 08/838,198, entitled "PHARMACEUTICAL GRADE BOTANICAL DRUGS", filed Apr. 15, 1997, chapter 28, pages 173–175, incorporated in its entirety by reference herein.

In this invention the active component(s) include, but are not limited to, one or more of the following chemical classes: acetogenins, alkaloids, carbohydrates, carotenoids, cinnamic acid derivatives, fatty acids, fatty acid esters, flavonoids, glycosides, isoprenoids, lipids, macrocyclic antibiotics, nucleic acids, penicillins, peptides, phenolics, polyacetylenes, polyketides, polyphenols, polysaccharides, proteins, prostaglandins, steroids and terpenoids.

The bioactivity/clinical indication for the St. John's Wort may be associated with a disease, disorder or condition of humans or other animals. Thus the methods are useful to produce pharmaceutical grade St. John's Wort for treatment and/or amelioration and/or prevention of human and/or veterinary diseases, disorders or conditions. Exemplary indications include, but are not limited to, a disorder induced by a microbial organism or a virus, mild to moderate depression, and to promote wound healing.

This invention also provides a method of preparing a PharmaPrint® for a pharmaceutical grade botanical, e.g., St. John's Wort. Furthermore, this invention provides for a pharmaceutical grade botanical, e.g., St. John's Wort prepared by the methods described herein.

3.1. DEFINITIONS

The term "pharmaceutical grade" when used in this specification means that certain specified biologically active and/or inactive components in a botanical drug must be within certain specified absolute and/or relative concentration range and/or that the components must exhibit certain activity levels as measured by a disease-, disorder- or condition-specific bioactivity assay. The disease, disorder or condition may afflict a human or an animal.

As will be understood by those skilled in the art, the term "pharmaceutical grade" is not meant to imply that the botanical drug is applicable only to products which are regulated for example those provided under prescription, i.e., "Rx" products or over the counter, i.e., "OTC". The term is equally applicable to products provided Rx, OTC or as a dietary supplement, i.e., "DSHEA".

As used herein "components" means discrete compounds (i.e. chemicals) which either are present naturally in a botanical drug or have been added to the botanical drug so as to prepare a pharmaceutical grade botanical drug having components within a defined bioactivity range(s) and/or compositional range(s).

As used herein "active components(s)" means one or more component(s) for which the summation of the individual component(s) activity in a disease-specific bioassay accounts for a substantial portion of the observed biological activity of the botanical material. Preferably, the summation of the active components' activities accounts for the majority or greater than 50% of the observed biological activity.

As used herein "fractions" typically means a group of components or class of structurally similar components having defined parameters such as solubility, molecular weight range, polarity range, adsorption coefficients, binding characteristics, chemical reactivity or selective solubility. Most frequently fractions will be the product of selective solvent solubility and partition techniques (i.e. liquid-liquid extraction) including pH dependent separations, chromatographic separation techniques, i.e., flash chromatography, preparative high performance liquid chromatography (HPLC), preparative gas chromatography, partition chromatography, preparative thin layer chromatography, affinity chromatography, size exclusion chromatography, liquid-liquid chromatography e.g., counter-current chromatography or centripetal or centrifugal chromatography.

The present invention may be understood more fully by reference to the detailed description of the invention and examples of specific embodiments in Sections below and the appended figures.

4. BRIEF DESCRIPTION OF THE DRAWINGS

Figure 4:
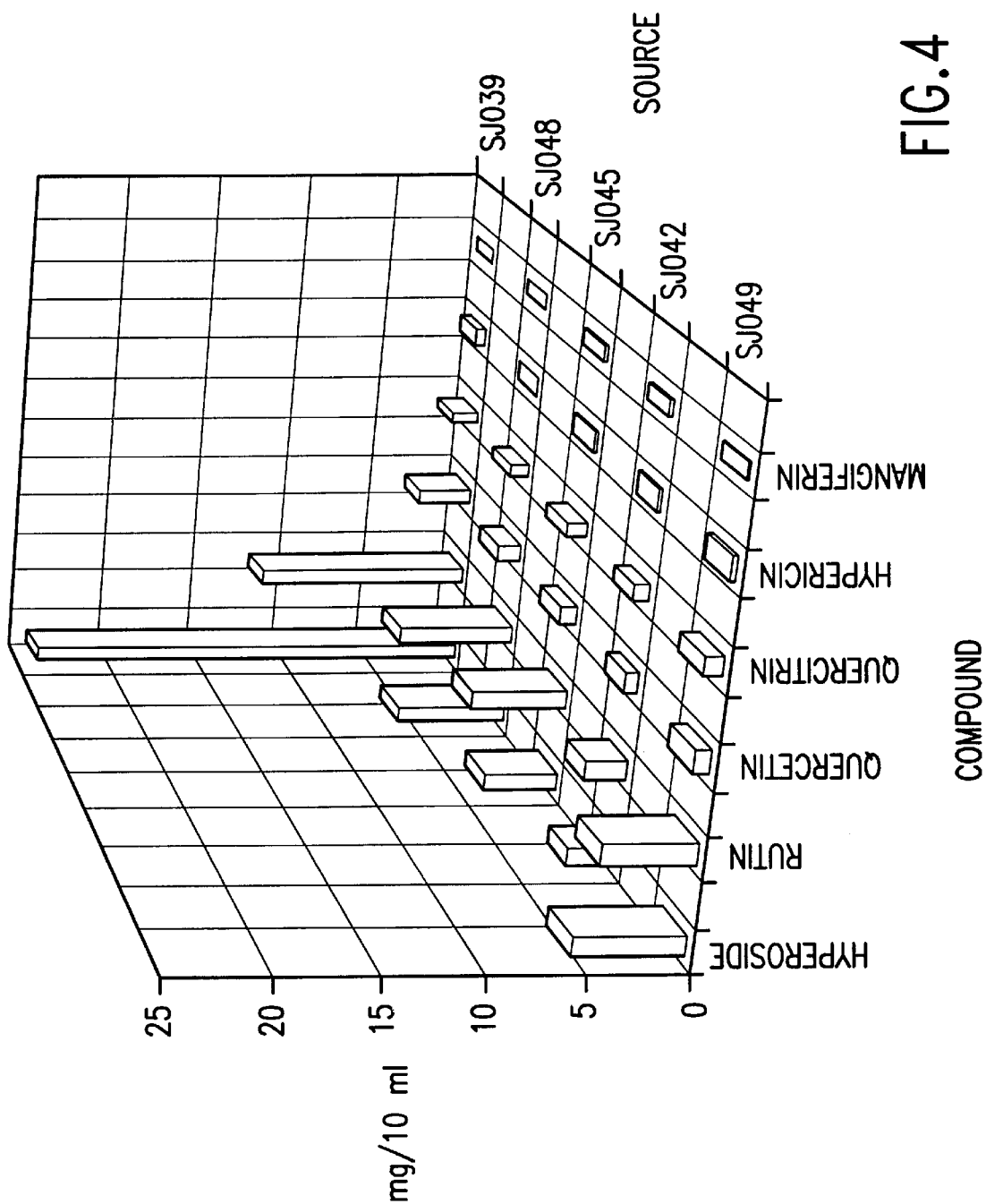

FIG. 4 shows the HPLC analysis for St. John's Wort. The vertical axis represents concentration (mg. per 10 ml) of product and the other axes depict the chemical compounds and indicate the commercial product.

Figure 5:
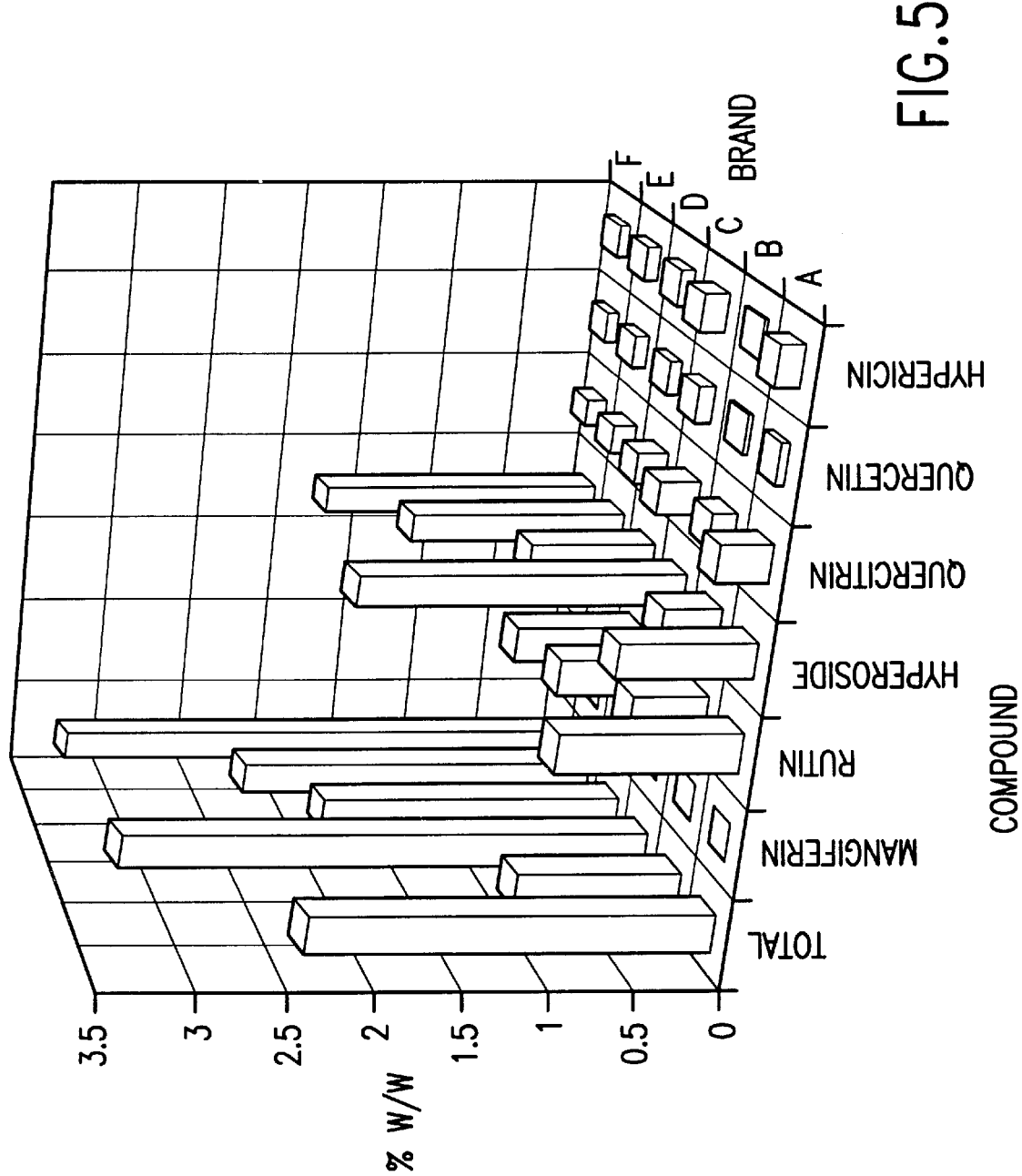

FIG. 5 shows additional HPLC analysis for St. John's Wort. The vertical axis represents concentration (mg. per 10 ml) of product and the other axes indicate the chemical compounds and the commercial product.

Figure 6:
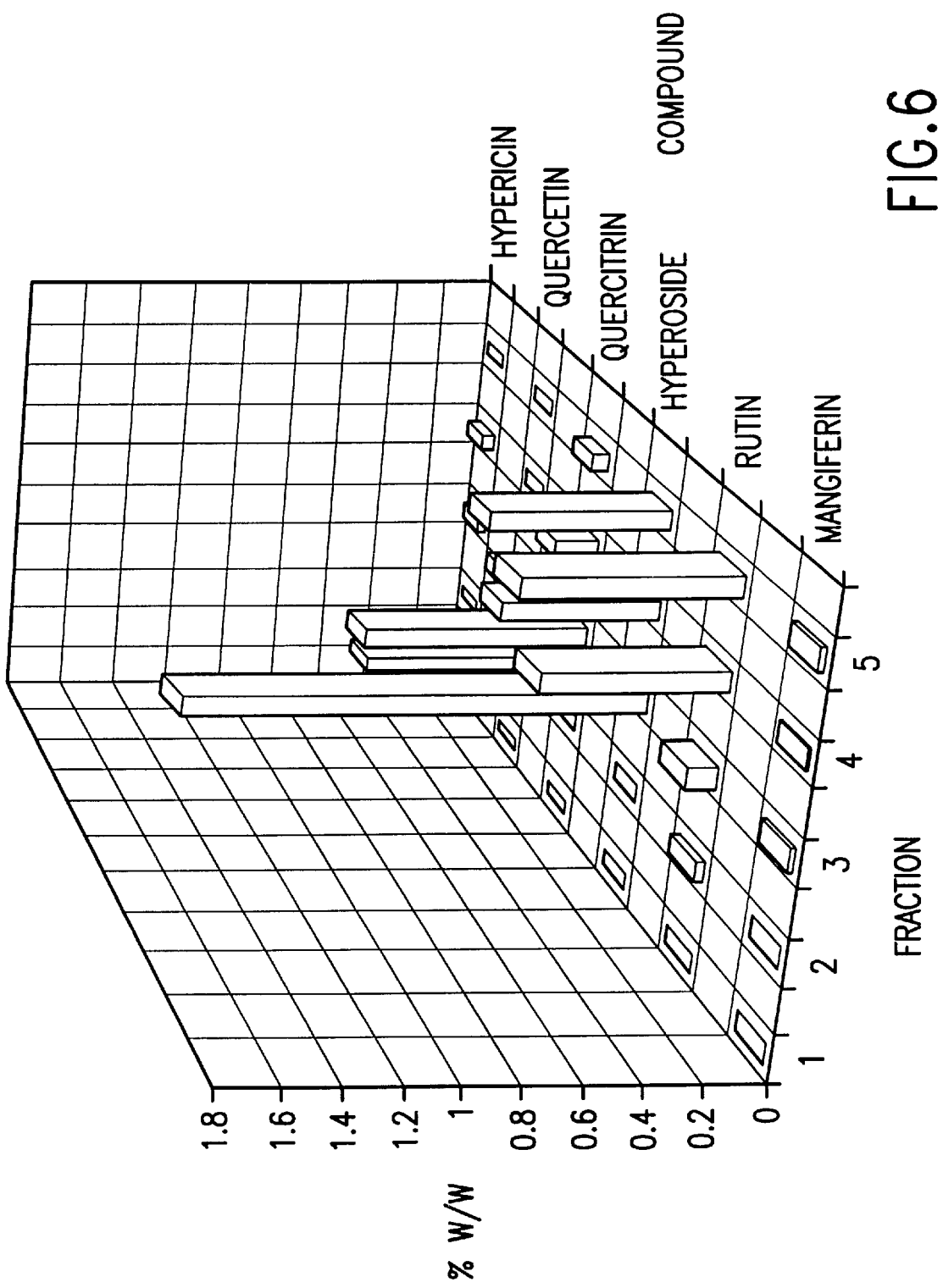

FIG. 6 shows fractional analysis for St. John's Wort. The vertical axis represents the concentration (mg. per 10 ml) of product and the other axes indicate the fractions and the commercial product.

5. DETAILED DESCRIPTION OF THE INVENTION

5.1. METHODS OF PHARMAPRINTING™

The present invention provides a method for producing botanical drugs which may be classified as being of pharmaceutical grade. The method is designated PharmaPrinting™. The pharmaceutical grade botanical drugs made by the method of the present invention are particularly well-suited for use in clinical studies and more importantly for use in treatment of patients. The method insures that the drug being used for a particular protocol will be of consistent quality and consistently suitable for use as human and veterinary prophylactic or therapeutic agents.

The present invention provides the ability to closely control the quality, dosage and clinical effectiveness of botanical extracts and other botanical materials, e.g., botanical of St. John's Wort. One aspect of the present invention involves the establishment of the chemical and/or bioactivity fingerprint standards for various botanical materials. Once established, the fingerprint standards are used in drug production procedures to insure that the botanical materials meet pharmaceutical grade requirements. Specific quantitative and biological fingerprints are presented which have been established for a number of botanical materials as a further aspect of the invention. These fingerprints are useful for determining if a particular botanical material meets levels of pharmacological activity and composition requirements for a particular treatment regimen. Such a determination is important to insure that clinical studies and patient treatment with the botanical materials are based on consistent and verifiable extract composition parameters. This invention is useful in providing botanical materials which are sufficiently characterized and whose compositions are consistent between batches, so that they can be precisely dosed and used effectively in clinical settings. The methods described herein provide an assurance that the results of a clinical trial will be reproducible.

Initially, a sample of the botanical material of interest is obtained. Many botanicals are commercially available as the raw material or as a processed extract. Often it is a botanical extract or other composition which is intended for use as a drug. The processed material may include a plurality of active components which exhibit a given biological activity and plurality of inactive components which do not directly exhibit the biological activity of interest. In one embodiment, an aliquot is removed from the botanical material and subjected to a quality assurance or standardization procedure. Preferably, the aliquot is a representative aliquot of a homogeneous botanical material. The procedure involves separating the aliquot of botanical material into a plurality of marker fractions wherein each of the marker fractions includes at least one of the active components or in some cases one of the inactive components. The amount of active component or inactive component in each of the marker fractions is determined in order to provide a quantitative fingerprint of the aliquot. The degree of biological activity for each of the marker fractions is also determined to provide a biological activity fingerprint for the aliquot. The chemical and/or biological activity fingerprints of the aliquot are then compared to corresponding fingerprints which have been established for a pharmaceutical grade drug. If the fingerprints of the botanical match the standard fingerprints, then the botanical is identified as a pharmaceutical grade botanical drug. If not, then the botanical may be modified so as to provide a match with the standard fingerprints or may be rejected.

5.1.1. METHODS OF DEVELOPING A PHARMAPRINT®

The method of developing a PharmaPrint® for a botanical when a range of putative active components is known begins with a literature review. It involves reviewing the chemical literature, the biological literature, the published bioassays and clinical data for the botanical. Particularly useful sources of information are the NAPRALERT computer database managed by Dr. Norman Farnsworth in the Program for Collaborative Research in the Pharmaceutical Sciences, University of Illinois, Chicago; Leung and Foster, *Encyclopedia of Common Natural Ingredients Used in Food, Drugs and Cosmetics*, 2nd Ed. John Wiley & Sons: New York, N.Y., 1996; *Herbal Drugs and Phytopharmaceuticals*, ed. N. G. Bisset, CRC Press: Boca Raton, Fla., 1994; Duke, *Handbook of Biologically Active Phytochemicals and Their Activities*, CRC Press: Boca Raton, Fla., 1992; Tyler and Foster "Herbs and Phytomedicinal Products" in *Handbook of Nonprescription Drugs* Berardi et al. eds., United Book Press, Inc.: Washington, D.C., 1996. For a given indication, the literature must be studied to confirm that the putative active components are actually associated with that disease state. In addition, if there are any bioassays known for the putative active components and known for the indication, the bioassays must be consistent with both the indication and the putative active components. The appropriate bioassay(s) is tied to a clinically relevant endpoint(s). The bioassay(s) should be quantitative over a wide concentration range. Typically, an $IC_{50}$ curve (Inhibitory Concentration 50%), $EC_{50}$ (Effective Concentration 50%), or an appropriate $K_i$ or $K_d$ (dissociation constant of the enzyme and its inhibitor) curve is prepared. A thorough chemical and biological analysis of both putative active components and chromatographic fractions of the botanical is then performed. The results are analyzed to prepare a quantitative analysis of the biological activity for each of the chemical components in the sample. Then, the bioactivity of the sample as a whole is compared to the bioactivity of the individual components. At this point the individual chemical components can be correlated with a clinically relevant endpoint. Similar methodologies may be applied to bioassays measuring stimulatory or inhibitory effects.

Based on activity of the components individually and knowing the total activity, the components should, when combined, account for a substantial portion of the biological activity. Generally, the combined activity will account for at least 25% of the total activity.

Preferably, the summation of the individual active components' activities account for the majority or greater than 50% of the observed biological activity. More preferably, the isolated individual components are responsible for more than 70% of the activity. More preferable still, the isolated individual components are responsible for greater than 80% of the biological activity.

Another consideration will be to select as few active components as possible to be part of the PharmaPrint™. Fewer active components are important for practical considerations in raw material acceptance and manufacturing. In this invention, a correlation is established between the relevant chemical components and the bioactivity. Once a satisfactory correlation is established, it may not be necessary to perform the biological fingerprints on each sample. Rather, a chemical analysis of the appropriate components and/or marker fractions of each sample of the botanical of interest will suffice to account for most of the biological activity and establish that a given botanical sample is pharmaceutical grade.

In one embodiment, the present invention may involve one of the following procedures. One procedure, as schematically outlined in FIG. 1, involves establishing the compositional and bioactivity fingerprint standards for a given pharmaceutical grade botanical drug. Once the fingerprint standards are established, then the actual processing of the botanical into a pharmaceutical grade drug can be carried out as schematically outlined in FIG. 2.

Figure 1:
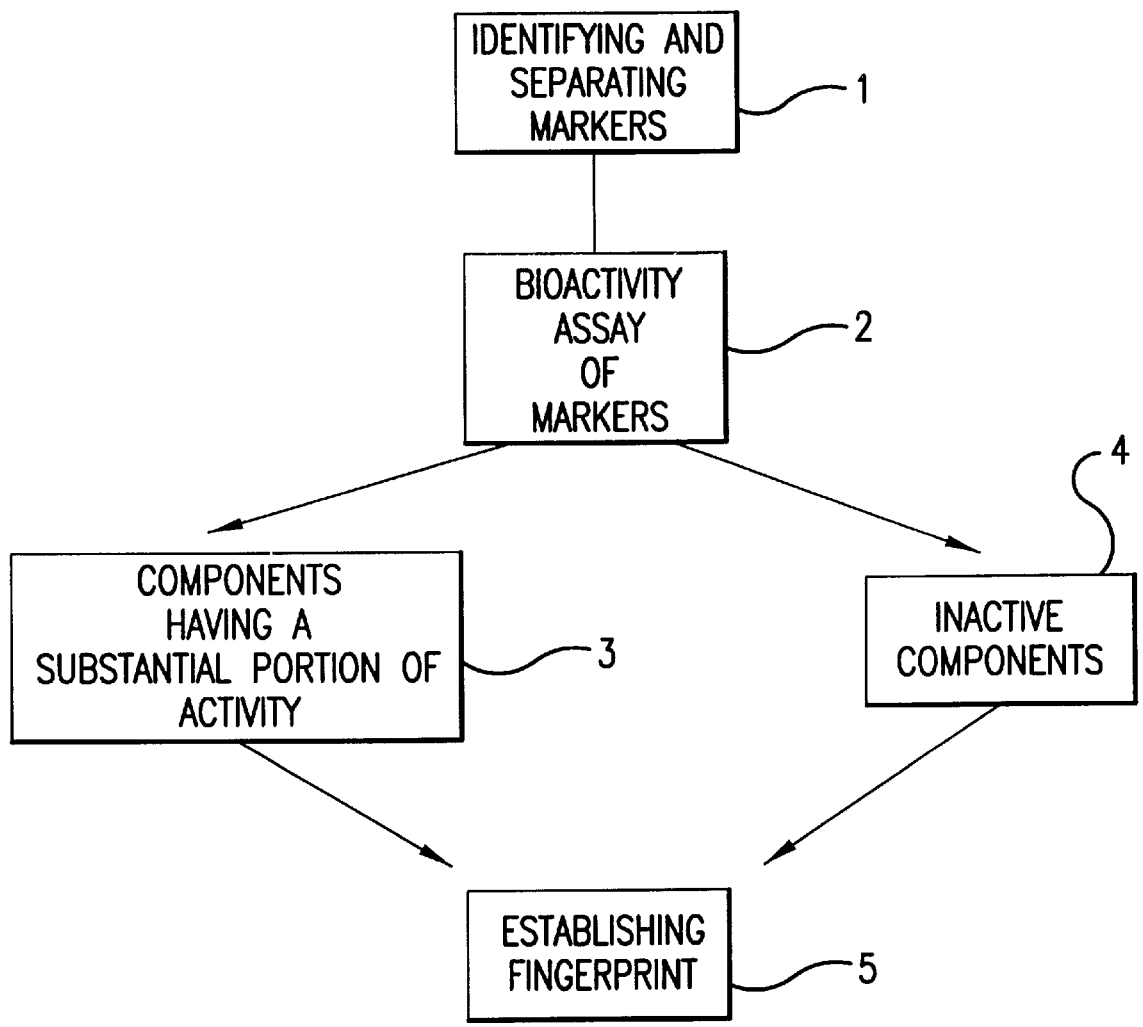
FIG. 1 is a schematic representation of a procedure in accordance with the present invention which is used to establish standard chemical and/or bioactivity fingerprints against which subsequent processed botanical materials are compared during production of pharmaceutical grade drugs.

The initial step in establishing the chemical and/or bioactivity fingerprint for a given botanical involves separating the extract or powder into one or more groups as represented by step 1 in FIG. 1. These groups are separated out and identified based on their potential as markers (which may or may not comprise active components) for the fingerprint which is to be established for the processed botanical material. The putative components or groups of putative components which are chosen and identified as potential markers will vary widely depending upon the botanical being processed and the pharmaceutical use. There should be at least two putative markers selected for each botanical. The number of potential markers may be more than five and can be as high 15 to 20 or more for complex botanical extracts or powders. The potential markers are identified and selected, for the most part, based on their potential biological activity or contribution to biological activity for a given pharmaceutical application. For a different indication the same botanical may be used for preparing an extract with a different extraction procedure in order to optimize specific bioactive constituents. Markers which have no apparent biological activity by themselves may be separated out and may be included as markers for use in the fingerprint. These "proxy" markers may be desirable as an internal standard where the markers' presence is indicative of other active components necessary to provide a substantial portion of the overall observed biological activity for the botanical drug. They also help to assure proper botanical identity of the drug (i.e. chemotoxonomy).

The initial separation of the botanical into various groups of putative markers is accomplished by conventional separation techniques ranging from simple extraction and partition, to complex affinity chromatographic techniques, including gel filtration chromatography, flash silica gel chromatography and reverse phase chromatography. Once the putative markers have been identified for a given botanical, then the bioactivity of each of the markers is determined as depicted by step 2 in FIG. 1. The particular bioassay used to determine bioactivity of the botanical is chosen based upon the intended use for the botanical. The bioassay preferably will provide a reflection of the putative markers' bioactivity with respect to the condition or indication which is to be treated with the botanical.

The bioassay results obtained in step 2 are used to identify the components having the desired bioactivity (step 3) and those which are less active or essentially inactive (step 4). Each of the groups identified in steps 3 and 4 is then analyzed quantitatively to determine the amount of each identified component present in each group. The results of the bioassays and quantitative compositional assays are then used to prepare a bioassay fingerprint and/or a chemical fingerprint for the botanical as depicted by step 5 in FIG. 1. As part of establishing the fingerprints for the botanical, acceptable ranges of bioactivity and/or chemical composition are determined. This is done primarily based upon establishing acceptable ranges of bioactivity and quantitative amounts for each marker which provide for the desired pharmacological activity of the processed material as a whole.

In addition, various combinations of active and inactive marker fractions may be evaluated to establish potential increases in desired bioactivity resulting from combinations of the active and inactive components.

The bioassay and quantitative fingerprints which are established in step 5 provide an accurate identification of the botanical which can be used in establishing the dosage regimens and treatment schedules which are necessary for clinical use. The dosage regimens and treatment schedules are established using conventional clinical methods which are commonly employed when investigating any new drug. The processed material which is used to determine the dosage and treatment schedules must be matched with and meet the requirements of the fingerprints established in step 5. This method insures that the dosage and treatment schedules are effective and reproducible since the processed materials used in the dosage and scheduling studies all have the same fingerprints in accordance with the present invention.

The bioassay and quantitative fingerprints which are determined by the general procedure as set forth in FIG. 1 are used as part of the manufacturing procedure for producing pharmaceutical grade botanical drugs. The fingerprints are used as part of a quality assurance or standardization procedure to insure that a given botanical contains the appropriate compounds and is processed correctly to provide a botanical drug which will perform the same clinically as the material which has been standardized and tested in accordance with the procedure set forth in FIG. 1.

Figure 2:
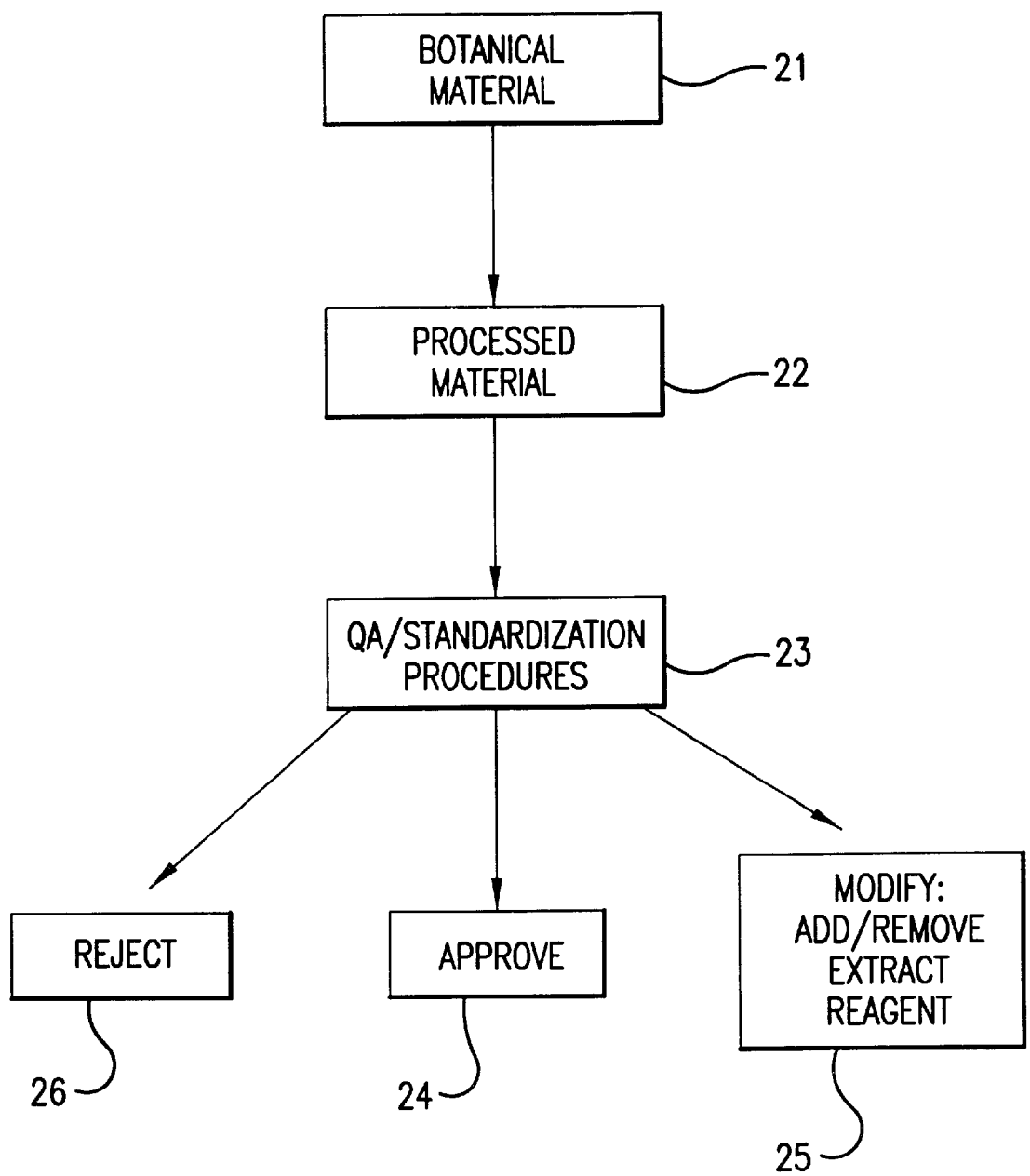
FIG. 2 is a schematic representation of a procedure in accordance with the present invention which is used to process botanical materials into pharmaceutical grade drugs.

An exemplary procedure for producing pharmaceutical grade botanicals in accordance with the present invention is shown schematically in FIG. 2. The botanical of interest 21 is first processed by extraction, powdering or other manufacturing process to form a processed botanical material 22. A sample of the processed material 22 is then analyzed to establish whether or not it matches the fingerprint requirements established during the standardization procedure of FIG. 1. This quality assurance or standardization procedure is depicted at 23 in FIG. 2. If the processed material meets the previously established fingerprint requirements for the particular material, then it is approved as being of pharmaceutical grade as represented by step 24. If the material is close, but does not quite match the standard fingerprint, then it is modified as required to match the fingerprint standards (step 25). The modification of the processed material to meet fingerprint standards may be done by a variety of ways. The methods of further processing botanicals may including additional extraction of the botanical, selective extraction, selective processing, recombination of batches (e.g. mixing high and low dose batches to prepare the pharmaceutical grade material) or the addition of various compounds, as required. If the botanical is substantially outside the fingerprint ranges for both bioactivity markers and quantitative markers, then the batch is rejected (step 26).

In one embodiment, the quality assurance standardization step 23 used to determine if a given botanical is pharmaceutical grade involves obtaining a uniform sample, preferably a homogeneous sample, or aliquot of the botanical which is to be tested. The sample should include the active components which contribute to the observed biological activity of the material and produce the bioactivity and/or chemical fingerprint of the previously determined standard. The sample will also include one or more inactive components. Inactive components are those which may not have a direct measurable biological activity. Inactive components include the following categories: components with activity so low that they do not account for a substantial portion of the activity; components whose presence indicates the presence of other bioactive components and can act as proxy markers for these components; inactive components that are chemically or biologically inactive in the relevant assays. The sample is preferably only a small aliquot of the botanical material being tested. Accordingly, it is important that a uniform sample, preferably a homogeneous sample, be obtained which is representative of the entire batch of material.

Figure 3:
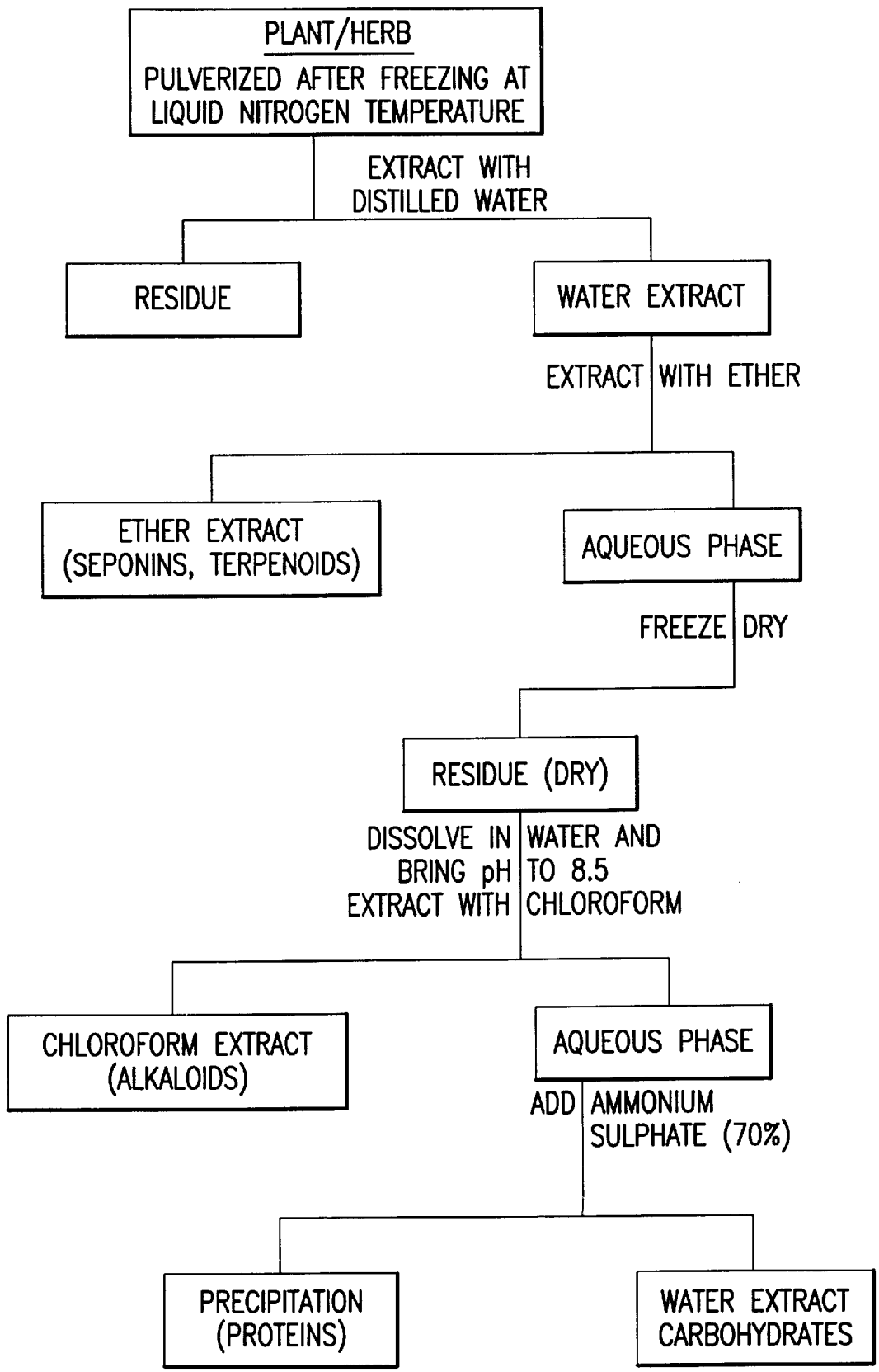
FIG. 3 is a schematic representation of a procedure for isolating different classes of biologically active components.

A more detailed schematic is shown in FIG. 3 showing the initial separation of the different components present in an aqueous extract of a botanical. Sequential extraction and precipitation are used to isolate the active components in either the aqueous or the organic phase. The scheme in FIG. 3 is particularly well suited for separating the classes of water-soluble active components from a botanical such as mistletoe.

An exemplary general method for separating plants into major classes of chemical components is set forth schematically in FIG. 3. Primarily fresh plants (including leaves, roots, flowers, berries and stems) should be used, although dried materials may also be utilized. Specific plant parts, such as the leaves, flowers, stems or root may be used if desired.

In this method the specific part or whole plant may be frozen at liquid nitrogen temperature. This facilitates grinding and also preserves the integrity and potency of the active components.

The pulverized powder is extracted with distilled water repeatedly. If desired, the extraction may be carried out with hot water, alcohol, other organic solvents, aqueous alcohol, dilute acetic acid or any combination thereof. The actual temperature chosen is preferably close to or at the boiling temperature of water. It is preferred that the overall bioactivity of the extract be initially determined. The combined extracts are subjected to a specific bioassay, e.g., a test for inhibiting the growth of bacteria in Petri dishes if the drug is to be used as an antibacterial. Alternatively, tests against cell cultures of cancer cells are conducted preferably if the drug is intended for use as an anticancer agent. From these data, bioactivity units contained in an extract per ml are calculated (bioactivity units are defined as the dilution number of this extract needed to inhibit 50% growth of bacterium or cancer cell in test system). Similarly bioactivity units for a stimulatory effect, e.g., immunostimulation can be calculated.

For establishing a pharmaceutical fingerprint (PharmaPrint®) in accordance with the present invention, the plant is extracted according to the procedure as set forth in FIG. 3 to separate it into major components (e.g. saponins, terpenoids, lipids, alkaloids, nucleic acids, proteins and carbohydrates). Each separated group of components is tested for bioactivity as needed. This may point to activity (e.g. in protein and alkaloid fractions as in *Viscum album*). The active class or classes of compounds are further separated into individual components by affinity chromatography, high performance liquid chromatography, gas chromatography or other chromatography. The components with major contribution towards biological activity are quantified on the basis of weight and specific bioactivity units. These components provide the fingerprint to establish the pharmaceutical requirements for the original herbal extract. The bioactivity units per ml of the pharmaceutical grade extract provide a way to establish exact dosage for clinical studies.

Once the sample is separated into individual marker fractions, and at least one having at least one active component, each fraction is analyzed to determine the amount of active component therein and provide a quantitative fingerprint of the sample. The quantitation of each fraction can be achieved using any of the known quantitative analysis methods. Exemplary quantitation methods include gravimetric analysis, spectral analysis or the use of quantitative detectors, such as those used in gas chromatography or high performance liquid chromatography and other separation systems. Other suitable quantitative analytical methods include analysis by enzymatic, radiometric, calorimetric, elemental analysis spectrophotometric, fluorescent or phosphorescent methods and antibody assays such as enzyme linked immunosorbant assay (ELISA) or radioimmunoassay (RIA).

In one embodiment, the results of the quantitative analysis of each fraction are used to prepare a quantitative fingerprint of the sample. The fingerprint is composed of the quantity of component in each of the marker fractions and the identity of the component. This quantitative fingerprint is then compared to the known standard fingerprint which has been established (FIG. 1) in order for the material to be considered as pharmaceutical grade. If the quantitative fingerprint of the sample falls within the range of quantities set forth for the pharmaceutical grade fingerprint, then the material may be identified as being of pharmaceutical grade.

As a further part of the quality assurance assay, the individual marker fractions may be subjected to biological assays. The biological assays which are used to test the various fractions are the same as those used for the standard fingerprint and will also depend upon the particular clinical use intended for the material.

The bioactivity fingerprint generated for the material is compared to the standard bioactivity fingerprint which has been established in order for the material to be considered as pharmaceutical grade. If the bioactivity fingerprint of the sample falls within the range of bioactivities set forth for the pharmaceutical grade fingerprint, then the material is identified as, and approved as, being of pharmaceutical grade.

5.1.2. ALTERNATIVE METHODS OF DEVELOPING A PHARMAPRINT®

The method of developing a PharmaPrint® for a botanical when the putative active components are not known also begins with a literature review. It involves reviewing any chemical literature, biological literature, published bioassays or clinical data available for the botanical, or related botanicals, or for botanicals with related activities. Based on the disease state, a series of relevant bioassays is chosen. The activity of the total sample or extract is analyzed using bioassays. Those bioassays that show activity are then used to analyze fractions of the botanical for which the putative active components are not yet known. The fractionation is based on the usual methods, e.g., separation by dielectric constant, biological affinity, polarity, size, solubility or absorptive power. The fractions are then analyzed to determine which fraction is responsible for the activity. Assuming activity is found, each active fraction is refractionated to isolate the individual putative active components, i.e., pure chemical compounds. Based on knowing the individual chemical compounds and knowing their quantitative biological activity, a quantitative potency curve may be drawn and the 50% inhibitory concentration ($IC_{50}$) for each individual chemical component may be determined. If the putative active components are agonists, then other parameters (binding, activation, response) may be needed. In the general case, the bioassay will consist of appropriate tests of the stimulatory or inhibitory effects of the constituents, fractions or entire extract, followed by an appropriate quantitative evaluation of those effects. For the most likely (or typical) assays in which a standard (or radiolabelled) agonist or antagonist causes a measurable effect, inhibition and/or stimulation by the subject material may be assessed and expressed typically via the determination of an $IC_{50}$, $EC_{50}$, etc. value, or other suitable measure (e.g., $K_i$, $K_d$, $K_m$, etc). The activities of individual putative active components are then totalled and that summation is compared to the activity in the unfractionated botanical sample. If these components account for a substantial portion of the activity, then one has an initial fingerprint of "active components" for the botanical where the active components were not known.

5.1.3 ADDITIONAL VARIATIONS ON THE METHOD OF DEVELOPING A PHARMAPRINT®

The general method outlined above for PharmaPrinting™ a botanical whose putative active components are not known has several variations should complications arise in the course of the analysis. One variation occurs when the summation of individual components do not account for a substantial portion of the biological activity of the botanical. At this point there are several likely reasons for the reduced activity of the individual components, one, decomposition or degradation of active components or, two, a synergistic effect. In another possible scenario there may be no significant or greatly lessened activity seen from any of the fractions, but the whole botanical or extract shows activity in the bioassay. Nonspecific matrix effects may also lessen the total extract activity, when compared to standards.

To determine if the active components are decomposing in the course of the assay is relatively simple. One merely recombines all of the fractions and compares the activity of the recombined fractions with the activity of the crude material. If substantial activity has been lost, then the problem is probably decomposition. To determine which active components may be decomposing, the chromatographic analysis of the crude botanical is compared with that of the recombined fractions. Peaks that are missing or are reduced in size indicate that components may be decomposing. To overcome decomposition many methods exist. Typically, milder extraction/fractionation methods such as liquid-liquid chromatography (counter-current chromatography) or supercritical carbon dioxide extraction or chromatography may be used.

Another explanation for the activity of the individual fractions not accounting for a substantial portion of the expected total activity is a synergistic effect between one or more active components with each other, or inactive components. To determine that a synergistic effect is taking place, pair-wise recombined fractions need to be analyzed. If the combined fractions show more activity than the individual fractions, two or more individual components in the fractions may be acting synergistically. For example, one may have three fractions, each alone responsible for 10% of the bioactivity (i.e., their uncombined additive bioactivity is 30%) but combined responsible for 100% of the activity. In that case the fractions are acting synergistically. By repeated pair-wise recombination of fractions or looking at larger fractions, any synergistic activity will be discovered. Once two fractions show synergy, they are then refractionated as above, and pairs of individual fractions or pairs of isolated components are studied to find the individual components that act synergistically. Three way comparisons of individual components or fractions may also be studied.

What if the fractions have no activity in the bioassay in which the botanical shows activity? Here, the explanations include decomposition, synergy, or many active components such that no individual fraction shows activity. The first step would be to fractionate each initial fraction and see if active components appear in the bioassay. It that does not succeed, the fractions should be recombined and assayed to determine if decomposition of the actives is taking place. If decomposition is taking place, the appropriate measures as described above should be taken. If there is no decomposition, then alternative methods of fractionation should be tried. Eventually, large enough or appropriately sized or selected fractions will show activity. If synergy is a suspected problem, then proceed as in the synergy section described above.

5.2. METHODS OF PROCESSING AND EXTRACTING BOTANICAL MATERIALS

The botanical material may be processed to form an aqueous or organic extract of the whole plant or a selected part of the plant. The botanical material can also be processed in whole or part to form a powder. Many of the botanicals of interest are commercially available as powders, aqueous extracts, organic extracts or oils. In one embodiment, extracts of the plant material are preferred because they are easier to dissolve in liquid pharmaceutical carriers. However, powdered plant materials are well-suited for many applications where the drug is administered in solid form, e.g., tablets or capsules. Such methods are well known to those of skill in the art. Furthermore, many of the plant materials and/or extracts are available commercially. As examples of the processing and extracting of botanicals the following examples are provided. Additional examples are provided in the detailed description.

For a typical root, it may be sliced, frozen or pulverized. If powdered it is then shaken with an appropriate solvent and filtered (Tanabe et al., 1991, *Shoyakugaku Zassi*, 45(4):316–320). Alternatively, the following methods are used: the root is homogenized, acetone extracted and filtered; the botanical may be steam distilled to obtain essential oils and the distillate dissolved in acetone-water or appropriate solvent; or the cut rhizomes are frozen and/or freeze-dried and the resulting powder acetone-water extracted (Tanabe et al., 1991, *Shoyakugaku Zassi* 45(4):321–326). Another method of processing botanicals is aqueous extraction with 100° C. water (Yamahara et al., 1985, *J. Ethnopharmacology* 13:217–225). The initial solvent extract from the methods above may be further extracted using liquid/liquid extraction with an appropriate solvent. The botanical may be extracted in two steps using polar and non-polar solvents respectively. The solvents are then evaporated and the fractions combined (Nagabhusan et al., 1987, *Cancer Let.* 36:221–233). Botanicals may also be processed as a paste or powder which may be cooked (Zhang et al., 1994, *J. of Food Science* 59(6):1338–1343).

A variety of solvents may be used to extract the dried botanicals, for example acetone, acetonitrile, dichloromethane, ethyl acetate, ethanol, hexane, isopropanol, methanol, other alcohols, and supercritical carbon dioxide (Sipro et al., 1990, *Int. J. of Food Science and Technology* 25:566–575 and references therein).

For other botanicals such as Saw Palmetto, the medicinal products are the seed oil or dried berries. In a typical preparation, a hexane or supercritical carbon dioxide extract is prepared. Many Saw Palmetto preparations are commercially available, for example Permixon™ or Talso™. For an example of supercritical carbon dioxide extraction of a botanical, see Indena, European Patent No. 0 250 953 B1. Alternatively, the botanical may be crushed and extracted with an appropriate solvent (90%) in a soxhlet (Elghamry et al., 1969, *Experientia* 25(8):828–829). The botanical may also be ethanol extracted (Weisser et al., 1996, *The Prostate* 28:300–306).

The dried material may be prepared in a variety of ways including freeze-drying, drying via microwave, cooling with liquid nitrogen and pulverizing; drying at 70° C. under vacuum for a duration of 10 hours; or air-drying in the shade, or with forced heated air (List and Schmidt, *Hagers Handbuch der Pharmazeutischen Praxis,* Springer-Verlag: New York, 1993, 1973–79; Araya et al., 1981, *Journal of Comparative Pathology,* 135–141). Teas, dilute aqueous extracts, also known as infusions, may be made in 60–100° C. water (Nosel and Schilcher, 1990). Decoctions may also be utilized. Extraction is more efficient when the particle size is less than 0.25 mm (List and Schmidt, *Phytopharmaceutical Technology,* CRC Press: Boca Raton, Fla., 1989).

Various guidelines are available for preparing oil extracts of botanicals. The botanical may be digested (macerated) in oil at 45° C. for 10 days, while others recommend 70° C. for 12–24 hours (Hobbs, 1989, *HerbalGram* 18/19:24–33; Smith et al., *Quality Validation Laboratory—Herb Pharm:* Williams, Oreg., 1996). In St. John's Wort for example, exposing the preparation to sunlight during the extraction process has been reported to result in a four-fold increase in flavonoid content calculated as quercetin (Maisenbacher and Kovar, 1992). Additionally, for St. John's Wort, two-fold increases of hypericin have been reported in oil preparations in which the material has been further extracted with alcohol, and mixed with the oil (Georgiev et al., 1983, *Nauchni Tr.-Vissh Inst. Plovid.* 30:175–183).

Alternatively an alcohol-water preparation may be prepared of the botanical (Dyukova, 1985, *Farmitsiya* 34:71–72; Georgiev et al., 1985, *Nauchni Tr.-Vissh Inst. Plovid.* 32:257–263; Wagner and Bladt, 1994, Kowalewski et al., 1981, *Herba Pol.* 27:295–302). According to *Hagers Handbuch* a tincture of a botanical, such as St. John's Wort, may be prepared by using drug or freezing ethanol soaked botanical materials, and filtering and preserving in dark bottles (List and Hörhammer, 1993).

Some botanicals, such as St. John's Wort, are both temperature and light sensitive. For this type of botanical the material should be dry packed with a refrigerant or shipped under refrigeration and protected from light and air. In St. John's Wort, hypericin content has been shown to drop significantly in powdered extract, tablet and juice preparations when stored at temperatures of 60° C.–140° C. for more than six weeks. Dry extracts stored at 20° C. were found to remain stable for at least one year (Adamski et al., 1971, *Farm. Pol.* 27:237–241; Benigni et al. *Hypericum. Plante Medicinali: Chimica, Farmacologia e Terapia*, Milano: Inverni & Della Beffa; 1971). Other St. John's Wort constituents, hyperforin and adhyperforin found in oil preparations are highly unstable, especially when exposed to light, and can degrade in as little as 14 days (Meisenbacher et al., 1992, *Planta Med.*, 351–354). Stability (in absence of air) was increased to six months in a preparation extracted with ethanol. Similarly, up to four xanthones and several flavonoids including quercetin and I3', II8-biapigenin have been detected suggesting these may be among the active constituents in external preparations (Bystrov et al., 1975, *Tetrahedron Letters* 32:2791–2794).

St. John's Wort is typically provided as a botanical material which may be derived from the stem, leaf, flowers, buds. The herb, or portions thereof, may also be in the form of a freeze dried powdered extract. An oil extract of the crushed flowers may be prepared. Various forms of infusions (aqueous), oil macerates, or alcohol water extractions are available.

5.2.1 LIQUID EXTRACTS OF PLANT MATERIALS AND POWDERED PLANT MATERIALS

St. John's Wort may be provided in the form of a liquid extract.

One common form of a liquid extract of botanical material is a "tea". A tea may be prepared through processes of infusion or decoction. Teas are generally an effective means to extract water soluble components from dried or fresh botanicals.

Another common form of liquid botanical extract is a tincture. A botanical tincture is typically an alcoholic or hydroalcoholic solution prepared from a fresh or dried botanical. It is usually prepared through a process of percolation or maceration.

Tinctures of potent botanicals, and homeopathic mother tinctures, may represent 10 g of botanical (dry weight) in 100 ml of tincture. Common botanicals have 20 g of botanical represented in 100 ml of tincture. The respective ratios of dried botanical to solvent for these preparations are 1:10 and 1:5, respectively. While these concentrations have been officially recognized by the U.S. National Formulary it has become common for tinctures to be prepared in 1:4, and other concentrations.

As compared to crude botanical extracts, tinctures may have a reduced microbial load and longer shelf life. This is largely due to the presence of alcohol at 20% or greater concentrations in the extract. Occasionally liquid extracts are made with glycerin and water as the solvent. These glycerites usually need to have at least 50% glycerin present to inhibit microbial contamination. Glycerites may also be prepared from tinctures by evaporating off alcohol and "back adding" glycerin in its place.

Another type of liquid extract is a "fluid extract". Fluid extracts are liquid preparations of botanicals that represent the medicinal properties of 1 g of dried botanical in 1 ml of extract. Official versions are made by the percolation process according to official monographs which determine the solvent to be used.

Liquid extracts that are concentrated, usually through evaporation of the solvent, may form extracts that are oily, semi-solid or solid in nature.

Dry powdered extracts may be prepared by the absorption of liquid extracts, oils, or semi-solids onto suitable carriers before solvent removal. Alternatively, dry powdered extracts may be prepared by direct removal of solvent from a liquid extract to provide a solid extract which can be powdered.

5.3 SEPARATION OF FRACTIONS

Once the sample extract has been prepared and/or alternatively purchased as a commercially available extract, a portion needs to be subjected to fractional analysis. If the fingerprint has already been established, the sample or aliquot is separated into the same plurality of marker fractions which are present in the standard fingerprint. Each of the marker fractions will include one or more of the active or inactive components. The marker fractions are established on an individual basis for each botanical material being tested. For some materials only a few marker fractions are required. For other more complex materials, there may be numerous marker fractions. For example in mistletoe, *Viscum album* L. protein extract, the preferred protein marker fractions are those fractions which are separated based on the sugar binding affinity of the fraction. However, different parameters for identifying and separating the materials into the marker fractions may be established based upon the types of components present in the botanical material. Separation of the sample into the marker fractions may be accomplished by any of the conventional separation techniques including liquid chromatography and extraction procedures. The same procedures which were used to establish the standard fingerprints should be used. Since the various fractions may be tested for biological activity, it is preferred that non-destructive separation techniques be utilized. Liquid column chromatography is a useful separation technique with affinity chromatography based on the specific binding ability of the compounds (e.g., carbohydrates and target enzymes) being particularly used.

After the fractionation, the solvent is removed and the material is dissolved in an appropriate medium for the bioassays. Examples of appropriate media include DMSO, ethanol, various detergents, water and an appropriate buffer. The choice of solvent will depend on the chemical nature of the component being analyzed and the compatibility with the assay system.

5.4 ESTABLISHMENT OF APPROPRIATE BIOASSAYS

Exemplary biological assays may include any cell proliferation assays, such as the measurement of L 1210 cell inhibition, immune activity or inhibition of critical enzyme which relates to specific diseases. Examples of other transformed cell lines which can be used for bioassays include HDLM-3 Hodgkin's lymphoma and Raji Burkitt's lymphoma, hepatoma cell line, primary or established cultures of human/animal cell lines which carry specific cell receptors or enzymes.

The results of the biological assays are used to prepare a bioactivity fingerprinting of the material. The fingerprint can be as simple as an assay of two selected marker fractions. Conversely, the fingerprint can include numerous different bioassays conducted on numerous different fractions. The same assay may be conducted on different marker fractions. Also, different assays may be conducted on the same marker fraction. The combination of bioassays will depend upon the complexity of the given botanical material and its intended clinical use. The bioassays will be the same as those conducted in establishing bioactivity fingerprint of the standard material.

5.4.1. ENZYMATIC AND RECEPTOR BASED ASSAYS

Enzymatic and receptor based assays are preferable in the practice of this invention. Assays are chosen either based on accepted enzymatic assays for a clinical disorder or they are chosen from relevant assays for a given clinical disorder. It is important to choose appropriate bioassay that may be validated. Ideally, a bioassay should be rugged, that is reproducible over time and show a quantitative dose response over a wide concentration range. An issue faced with a botanical for which the active components are not known is the choice of a relevant bioassay. Here, the human therapeutic use will serve as a guide to pick assays known in the art based on possible mechanisms of action. The mechanism of action should be consistent with a clinically relevant endpoint. There are a wide array of clinically relevant assays based on enzymatic activity, receptor binding activity, cell culture activity, activity against tissues and whole animal in vivo activity.

This section will address enzymatic and receptor binding assays. There are many books on enzymatic or receptor assays, for example, *Methods in Enzymology* by Academic Press or Boyers, *The Enzymes. Bioactive Natural Products, Detection, Isolation, and Structural Determination*, S. M. Colegate and R. J. Molyneux, CRC Press (1993), also discusses specific bioassays. *Methods in Cellular Immunology*, R. Rafael Fernandez-Botran and V. Vetvicka, CRC Press (1995) describes assays from immune cell activation and cytokine receptor assays. "Screening Microbial Metabolites for New Drugs-Theoretical and Practical Considerations" describes additional methods of finding pharmaceutically relevant bioassays (Yarbrough et al. (1993) *J. Antibiotics* 46(4):536–544). There are also many commercial contract research vendors, including Panlabs, Paracelsian and NovaScreen.

For example, for a botanical useful for treating neurological disorders, the array of bioassays might include adrenergic receptors, cholinergic receptors, dopamine receptors, GABA receptors, glutamate receptors, monoamine oxidase, nitric oxide synthetase, opiate receptors, or serotonin receptors. For cardiovascular disorders the array of assays may include adenosine $A_1$ agonism and antagonism; adrenergic $\alpha_1$, $\alpha_2$, $\beta_1$ agonism and antagonism; angiotensin I inhibition; platelet aggregation; calcium channel blockade; ileum contractile response; cardiac arrhythmia; cardiac inotropy; blood pressure; heart rate; chronotropy; contractility; hypoxia, hypobaric; hypoxia, KCN; portal vein, potassium depolarized; portal vein, spontaneously activated; or thromboxane $A_2$, platelet aggregation. For metabolic disorders the following bioassays may be used: cholesterol, serum HDL, serum total; serum HDL/cholesterol ratio; HDL/LDL ratios; glucose, serum—glucose loaded; or renal function, kaluresis, saluresis, and urine volume change. For allergy/inflammation disorders the following bioassays may be used: allergy, Arthurs reaction, passive cutaneous anaphylaxis; bradykinin $B_2$; contractility, tracheal; histamine $H_1$ antagonism; inflammation, carrageenan affects on macrophage migration; leukotriene $D_4$ antagonism; neurokinin $NK_1$ antagonism; or platelet activating factor, platelet aggregation or induction of biosynthesis of important inflammatory mediators (e.g. interleukins IL-1, IL-6, tumor necrosis factor or arachidonic acid). For gastrointestinal disorders the following bioassays may be used: cholecystokinin $CCK_A$ antagonism; cholinergic antagonism, peripheral; gastric acidity, pentagastrin; gastric ulcers, ethanol; ileum electrical stimulation modulation; ileum electrical stimulation spasm or serotonin 5-$HT_3$ antagonism. For antimicrobial, antifungal, or antitrichomonal disorders the following are used: *Candida albicans; Escherichia coli; Klebsiella pneumonaie; Mycobacterium ranae; Proteus vulgaris; Pseudomonas aeruginosa; Staphylococcus aureus*, methicillin resistant; *Trichomonas foetus*; or *Trichophyton mentagrophytes*. For other indications, one of skill in the art would be able to choose a relevant list of bioassays.

Specific examples of assays based on enzymes or receptors include the following: acetyl cholinesterase; aldolreductase; angiotensin converting enzyme (ACE); adrenergic $\alpha$, $\beta$, rat androgen receptor; CNS receptors; cyclooxygenase 1 or 2 (Cox 1, Cox 2); DNA repair enzymes; dopamine receptors; endocrine bioassays, estrogen receptors; fibrinogenase; GABA A or GABA B; $\beta$-glucuronidase; lipoxygenases, e.g., 5-lipoxygenase; monoamine oxidases (MAO-A, MAO-B); phospholipase $A_2$, platelet activating factor (PAF); potassium channel assays; prostacyclin cyclin; prostaglandin synthetase; serotonin assays, e.g., 5-HT activity or other serotonin receptor subtypes; serotonin re-uptake activity; steroid/thyroid superfamily receptors; thromboxane synthesis activity. Specific enzymatic assays are available from a variety of sources including Panlabs™ Inc (Bothell, Wash.) and NovaScreen™ (Baltimore, Md.). Additional assays include: ATPase inhibition, benzopyrene hydroxylase inhibition, HMG-CoA reductase inhibition, phosphodiesterase inhibition, protease inhibition, protein biosynthesis inhibition, tyrosine hydroxylase and kinase inhibition, testosterone-5$\alpha$-reductase and cytokine receptor assays.

5.4.2 CELL CULTURE AND OTHER ASSAYS

In addition to the enzymatic and receptor assays, there are also other biological assays. Preferably, these assays are performed in cell culture but may be performed on the whole organism. Cell culture assays include activity in cultured hepatocytes and hepatomas (for effect on cholesterol levels, LDL-cholesterol receptor levels and ratio of LDL/HDL cholesterol); anti-cancer activity against L 1210, HeLa or MCF-7 cells; modulating receptor levels in PC12 human neuroblastoma cells; modulation of primary cell culture activity of luteinizing hormone (LH), follicle stimulating hormone (FSH) or prolactin; $Ca^{2+}$ influx to mast cells; cell culture assays for phagocytosis, lymphocyte activity or TNF release; platelet aggregation activity or activity against HDLM-3 Hodgkin's lymphoma and Raji Burkitt's lymphoma cells, antimitotic activity, antiviral activity in infected cells, antibacterial activity (bacterial cell culture) and antifungal activity. Tissue or whole animal assays may also be used including anti-inflammatory mouse ear dermatitis, rat paw swelling; muscle contractility assays; passive cutaneous anaphylaxis; vasodilation assays; or whole animal carbon clearance tests. These assays are available from a variety of sources including Panlabs™ Inc. (Bothell, Wash.).

5.4.3. ANTICANCER ACTIVITY

The anticancer effects of drug can be studied in a variety of cell culture systems; these include mouse leukemias, L 1210, P388, L1578Y etc. Tumor cell lines of human origin like KB, and HeLa have also been used. In a typical assay tumor cells are grown in an appropriate cell culture media like RPMI-1640 containing 10% fetal calf serum. The logarithmically growing cells are treated with different concentrations of test material for 14–72 hours depending upon cell cycle time of the cell line. At the end of the incubation the cell growth is estimated by counting the cell number in untreated and treated groups. The cell viability can be ascertained by trypan blue exclusion test or by reduction of tetrazolium dyes by mitochondrial dehydrogenase. The ability of a drug to inhibit cell growth in culture may suggest its possible anticancer effects. These effects can be verified in animals bearing tumors, which are models for human disease (Khwaja, T. A., et al. (1986) Oncology, 43 (Suppl. 1): 42–50).

The most economical way to evaluate the anticancer effects of an agent is to study its effects on the growth of tumor cells in minimum essential medium (MEM) containing 10% fetal calf serum. The drug-exposed cells (in duplicates) are incubated in a humidified $CO_2$ incubator at 37° C. for 2–4 days, depending upon the population-doubling time of the tumor cells. At the end of the incubation period the cells are counted and the degree of cell growth inhibition is calculated from a comparison with untreated controlled cells grown under identical conditions. The type of cell lines used have varied from laboratory to laboratory depending upon individual needs. The National Cancer Institute (NCI) in the United States recommends the use of KB cells (a human nasopharyngeal carcinoma) for the evaluation of anticancer drugs in vitro. The cell growth inhibition is determined by estimating the protein content (Lowry's method) of the drug-treated and untreated controls. NCI has also recommended the use of suspension culture of mouse leukemia P388 for the evaluation of anticancer potential of plant extracts and related natural products.

Mouse leukemia L1210 cells, cultured in microtiter plates are routinely used for in vitro assays for anticancer activity. The cell population-doubling time of leukemia L1210 is 10–11 h and a drug exposure of 48 h (3–4 generations of logarithmic growth) is used for the evaluation of its antitumor activity. For growth inhibition studies all stock solutions and dilutions are made with sterile 0.9% NaCl solution. The cell cultures are seeded at $2-5 \times 10^4$ cells/ml in duplicates for each inhibitor concentration in a microtiter place (0.18 ml/well). The inhibitors are added in 0.02 ml volume to achieve 1:10 dilutions in each case. The covered microtiter plate is incubated for 48 h in a humidified $CO_2$ incubator containing 5% $CO^2$ in air. At the end of the incubation period aliquots of each well are added to a measured volume of isotonic saline and counted in an electronic cell counter. The cell viability is determined by trypan blue exclusion. The results are calculated by plotting percent cell growth inhibition (as compared to cell density of the saline-treated controls) versus log of drug concentration and expressed as the concentration which caused 50% inhibition in cell growth ($IC_{50}$) as determined from the graph.

The cytotoxic effects of a drug on a tumor cell line may also be evaluated. However, these experiments require longer periods of time to study and are more expensive. In these studies drug-treated cells are washed free of drug and then plated in soft agar or an appropriate medium and the cellular viability is estimated by the ability of the surviving cells to multiply and form microscopic colonies. The number of cellular colonies obtained with certain drug concentrations is compared with those obtained from untreated controls to evaluate cell kill or cytotoxic activity. In studies with mistletoe extract we have used loosely adherent cultures of EMT-6 cells (a mouse mammary adenocarcinoma). These cells are grown in Eagle's MEM (F14) containing 10% dialyzed fetal calf serum and antibiotics. The cell suspension is spun and the pellet suspended in Spinner's medium supplemented with 10% dialyzed fetal calf serum (70 cells/ml), plated in plastic Petri dishes and incubated for 2 h to permit cells to attach. At this time cells are exposed to various concentrations of extract for 2–24 h. Then, the medium is removed and replaced with drug-free medium and the dishes incubated for 5–7 days. The colonies are stained with methylene blue (0.33% in 0.01% KOH) and counted with an automatic colony counter. The plating efficiency of EMT-6 cells is 46%. (Khwaja et al., 1986, Oncology, 43(Supp. 1):42–50).

5.4.4. ANTIVIRAL ACTIVITY

The antiviral activity of different drugs can be ascertained in cell culture of human cell lines like HeLa or H9 lymphoma cells. These cells are infected with virus and the virus is allowed to propagate in cell cultures. The ability of virus to produce cell lysis or cytopathic effects is taken as the end point. For example, HIV infection of H9 cells results in production of multinucleated cells. These cytopathic effects, if reduced or eliminated by certain concentrations of the drug, indicates its potential as an anti-HIV agent. These results can be validated by estimation of viral enzyme in the cell cultures, e.g., by studying the amount of the expression of viral reverse transcriptase. A decreased expression of the viral enzyme would support antiviral effect of the drug treatment (Khwaja, T. A. U.S. Pat. No. 5,565,200; J. Levy et al. 1984, Science 225: 840).

5.5. ANALYTICAL METHODS FOR ANALYZING CHEMICAL COMPONENTS

There are many methods to separate and analyze individual chemical components including gas chromatography (GC), mass spectroscopy (MS), GC-MS, high performance liquid chromatography (HPLC), HPLC-MS, thin layer chromatography (TLC), high performance TLC (HPTLC) gel chromatography and reverse phase chromatography (RPC). These chromatographic methods may be performed either on an analytical scale or a preparative scale. To determine the actual chemical structure of unknown components, nuclear magnetic resonance (NMR) and mass spectrum fragmentation analysis are typically used.

The determination of the type of chromatography will depend on the chemical components most likely responsible for the bioactivity. For example if the bioactivity is likely due to fatty acids, the fatty acids are esterified and the esters analyzed on a GC. For organic compounds with alcohol groups, they are modified to prepare ethers, silyl derivatives or other less polar functional groups. These derivatives are then suitable for analysis by GC (Steinke et al., 1993, *Planta Med.* 59:155–160; Breu et al., 1992, *Arzneim.-Forsch/Drug Res.* 42(1):547–551). If the activity is most likely due to flavonoids, HPLC is the method of choice. Reverse-phase HPLC (RP-HPLC) has been used to analyze flavonoids from a variety of botanicals, specifically hawthorn, passion flower, chamomile, ginkgo (Pietta et al., 1989, *Chromatographia* 27(9/10):509–512). Plant constituents have been quantitatively determined by TLC (Vanhaelen and Vanhaelen-Fastre, 1983, *J. Chromatography* 281:263–271) as well as MS-analysis for garlic. CRC Handbooks of Chromatography on "Analysis of Lipids", K. D. Mukherjee, "Analysis and Characterization of Steroids", H. Lamparczyk, J. Sherma, and "High-Performance Liquid Chromatography of Peptides and Proteins", C. T. Mant and R. S. Hodges, are available and describe columns and solvent systems.

5.6. ANALYSIS OF FRACTIONS

In an alternative embodiment, rather than base the pharmaceutical fingerprint (PharmaPrint®) on discrete chemical components of known bioactivity, one may also establish the PharmaPrint® using defined fractions or classes of compounds. Some chemical constituents in botanicals form such a complex mixture of closely-related components that, from a practical point of view, it is desirable to base the PharmaPrint® on fractions or classes of components rather than on individual components. Examples of these types of components are lectins (sugar-binding proteins) or glycoproteins as well as the silymarins in milk thistle. There are many examples of fractional analysis (*Gel Filtration Principles and Methods* Pharmacia Biotech, Rahms i Lund: Sweden; Utsumi et al., 1987, *J. Biochem.* 101:1199–1208).

5.7. METHODS OF USE OF PHARMAPRINTED™ MATERIALS

After the botanical material has an established fingerprint, individual samples are then analyzed to determine if they fall within the accepted standards. Once the sample has been approved it is suitable for a variety of diseases relevant to humans and animals. Such materials are useful in clinical trials so as to provide materials of consistent quality and precise dosage formulations for trials. The PharmaPrinted™ material is also useful for toxicological tests in animals where once again the consistency of the material is useful for quantitative toxicological analysis. In many cases it would be of use as a reference material for analytical or biological use.

The PharmaPrinted™ botanical materials are useful for any disease state for which a botanical drug is associated. See for example Leung and Foster, 1996 and *Herbal Drugs and Phytopharmaceuticals,* 1994. More specific examples of disease states or therapeutic indications include AIDS, adaptogen, mild-to-moderate depression, anti-arthritic, anti-cancer, anti-diarrhetic, anti-helmenthic, anti-inflammatory, anti-nausea via GI, anti-rheumatic, anti-spasmodic, anti-ulcer, angina, antibacterial, antimutagenic, antioxidant, antiviral, arteriosclerosis, arthritis, asthma, blood pressure, benign prostatic hyperplasty (BPH), bronchial asthma, bronchitis, calmative, cough, cerebral circulatory disturbances, cholesterol lowering, cirrhosis, dermatological anti-inflammatory, diabetes, diuretic, drastic cathartic, dysmenorrhea, dyspepsia, emphysema, environmental stress, expectorant, free radical scavenger, GI distress, hemorrhoids, hepatitis, hepatoprotective, hypertension, hyperlipidemia, hyperprolactinemia, immunomodulatory activity, increase fibrinolysis, resistance to bacterial infection, inflammation, insomnia, lactation, liver protection, longevity, menstrual cycle regulation, migraine, muscle pain, osteoarthritis, pain, peripheral vascular disease, platelet aggregation, PMS, promote menstrual flow, prostatic disorders, reduce triglycerides, relieve menstrual pain, respiratory tract infections (RTI), retinopathy, sinusitus, rheumatism, sedative, sleep-promoting agent, sore throat, stimulate hair growth, superficial wound healing, tinnitus, topical eczema (dermatitis), urinary tract infection (UTI), varicose veins, venous insufficiency or wound healing.

Other indications include anti-hemorrhagic, anti-microbial, anti-parasitic, anti-pyretic, cardiotonic, carminitive, cholagogue, demulcent, diaphoretic, emetic, emmenagogue, emollient, febrifuge, galactagogue, hepatic, hypnotic, laxative, nervine, pectoral, rubefacient, stimulant, tonic, vulnerary, canker stores, pyorrhea, gingivitis, gastritis, ulcers, gallstones, intermittent claudication, cold, influenza, laryngitis, headache, shingles, cystitis, kidney stones, atopic vaginitis, uterine fibroids, osteoporosis and gout.

The pharmaceutical grade St. John's Wort prepared according to the methods of the present invention is indicated for alleviation of mild to moderate depression and headache, including tension headaches. In addition, the pharmaceutical grade St. John's Wort is indicated for anti-viral and anti-microbial indications. Further, the pharmaceutical grade St. John's Wort is useful to promote wound or burn healing.

5.8. PHARMAPRINT® OF ST. JOHN'S WORT

5.8.1. BIOLOGICAL PHARMAPRINT®

Exemplary biological PharmaPrint® values, derived using the methods described herein, are shown in Table 1. See, infra, Section 6.4 for a detailed discussion and explanation of each of the biological assays for each of the values presented in Table 1.

Values for each bioassay are expressed as a percentage range of inhibition at $10^{-4}$M unless otherwise indicated. Calculations for extracts and fractions are based on an assumption of an average molecular weight of 200.

TABLE 1

| | | | | BIOLOGICAL PHARMAPRINT ® VALUES* | | | | |
|---|---|---|---|---|---|---|---|---|
| EXTRACTS | $GABA_A$ | $MAO_A$ | NOS | Agonist NMDA | $Musc_{M1}$ Binding | AD,NS | Opiate NS | Sero |
| TOTAL ACTIVITY | 95 ± 20<br>95 ± 20<br>≧50%<br>at $10^{-5}$ | 25 ± 15 | 30 ± 15 | 40 ± 20 | 50 ± 20<br><br>≧20%<br>at $10^{-5}$ | 30 ± 15 | 20 ± 10 | 30 ± 15 |
| MARKER FRACTIONS | | | | | | | | |
| Fraction 1 | | 40 ± 20 | | 45 ± 20 | | 30 ± 15 | 60 ± 20 | |
| Fraction 2 | | 40 ± 20 | | | | 30 ± 15 | 40 ± 20 | |
| Fraction 3 | | 30 ± 15 | | | | | 20 ± 10 | |
| Fraction 4 | | | | | | | | |
| Fraction 5 | | | | | | 30 ± 15 | | |

TABLE 1-continued

BIOLOGICAL PHARMAPRINT ® VALUES*

| | GABA$_A$ | MAO$_A$ | NOS | Agonist NMDA | Musc. M1 | AD,NS | Opiate NS | Sero |
|---|---|---|---|---|---|---|---|---|
| Fraction 6 | | | | | | 30 ± 15 | | |
| Fraction 7 | 40 ± 20 | | | | 20 ± 10 | 30 ± 15 | | |
| Fraction 8 | 30 ± 15 | | | | | | | |
| Fraction 9 | 100 ± 20 | | | | | | | |
| Fraction 10 | 100 ± 20 | | | 35 ± 15 | | | | |
| REFERENCE COMPOUNDS | GABA$_A$ | MAO$_A$ | NOS | Agonist NMDA | Musc. M1 | AD,NS | Opiate NS | Sero |
| Hypericin | 30 ± 15 | | | | 80 ± 20 | 70 ± 20 | 70 ± 35 | **4 μM/51 ± 2 |
| Quercetin | | 10 ± 5 | | | | 30 ± 15 | | |
| Quercetrin | | | | | | 45 ± 20 | | 40 ± 20 |

**IC$_{50}$ data shown in addition to % inhibition activity 10$^{-4}$ M
*GABA$_A$, gamma amino butyric acid assay; MAO$_A$, monamine oxidase; NOS, nitric oxide synthetase; Agonist NMDA, activity against the glutamate receptor with N-methyl-D-aspartic acid (NMDA) control; Musc$_{M1}$ Binding, inhibition of binding of pinrenzepine to the muscarinic M1 receptor; AD, NS, adenosine receptor, non-specific Opiate NS, non-specific binding to the opiate receptor, Sero, serotonin reuptake assay.

By way of example, using the values in Table 1, the PharmaPrint® is based on the bioactivity of extract in the GABA$_A$ assay and one or more assays selected from MAO$_A$, monamine oxidase; NOS, nitric oxide synthetase; NMDA, activity against the glutamate receptor with N-methyl-D-aspartic acid (NMDA) control; Musc$_{M1}$, inhibition of binding of pinrenzepine to the muscarinic M1 receptor; AD, NS, adenosine receptor, non-specific; Opiate NS, non-specific binding to the opiate receptor; sero, serotonin reuptake assay.

In an alternative embodiment, the PharmaPrint® may be developed based on bioactivity equal to or greater than the lower end of the range of bioactivity values such as shown in Table 1. As an illustrative example of this embodiment, the PharmaPrint® value based on the bioactivity of total extract in the MUSC$_M$, assay (50±20) would be at least 30% inhibition on at 10$^{-4}$M.

5.8.2. CHEMICAL COMPONENTS

A review of the relevant literature relating to St. John's Wort reveals five marker compounds illustrated below in Table 2. See, infra, Section 6.5 for a detailed discussion and explanation of the selection of the chemical compounds. Table 3 presents the only two marker compounds (hypericin and guercitin) showing relevant biological activity.

TABLE 2

CHEMICAL COMPONENTS
St. John's Wart Extract & Capsules

| COMPOUND | BROAD RANGE | PREFERRED RANGE ± 2 MEAN ± 2 STD | MEDIUM RANGE |
|---|---|---|---|
| Rutin | 0.01 to 10% w/w | 0.05 to 3.11% w/w | 0.02 to 5.0% w/w |
| Hyperoside | 0.01 to 15% w/w | 0.05 to 3.96% w/w | 0.2 to 10% w/w |
| Quercetrin | 0.01 to 5.0% w/w | 0.13 to 0.33% w/w | 0.05 to 2.0% w/w |
| Quercitin | 0.001 to 10% w/w | 0.01 to 1.0% w/w | 0.005 to 5% w/w |
| Hypericin | 0.001 to 2.0% w/w | 0.01 to 0.13% w/w | 0.005 to 0.6% w/w |
| Fraction SJ-910-7 | <3.4% of Total Extract w/w | | |

TABLE 3

CHEMICAL PHARMAPRINT
Pharmaprint Range of Actives

| COMPOUND | BROAD RANGE | PREFERRED RANGE ± 2 MEAN ± 2 STD | MEDIUM RANGE |
|---|---|---|---|
| Hypericin | 0.001 to 2.0% w/w | 0.01 to 0.13% w/w | 0.005 to 0.6% w/w |
| Quercitin | 0.001 to 10% w/w | 0.01 to 1.0% w/w | 0.005 to 5% w/w |

5.8.3. CONVERSION RATIO

PharmaPrint® values developed using dry powdered extracts of a botanical material can be converted to values relevant to dry weight of raw botanical material using the ratios illustrated in Table 3 below. Thus, to convert PharmaPrint® values based on a dry powdered extract to values relevant to a dried plant material, one would divide by the appropriate factor in Table 4.

TABLE 4

CONVERSION RATIOS

| Botanical | Ratio (powder to extract) |
|---|---|
| Saw Palmetto | 10:1 |
| St. John's wort | 5:1 |
| Valerian | 5:1 |
| Echinacea | 5:1 |
| Ginkgo | 50:1 |
| Ginseng | 5:1 |
| St. John's Wort | 10:1 |
| Black Cohosh | 1:1 |
| Bilberry | 100.1 |
| Milk Thistle | 40:10 |

The following example is presented for purposes of illustration only and is not intended to limit the scope of the invention in any way.

6 EXAMPLE

ST. JOHN'S Wort, *Hypericum perforatum*

6.1 COMMERCIAL SUPPLIERS/PRODUCT NAMES

There are many commercial suppliers of St. John's Wort and extracts of St. John's Wort, including the following:

Jarsin™, Jarsin™ 300 (LI160) (Lichtwer Pharma GmbH, Berlin), Psychotonin™ M, Psychotonin™ forte (Hersteller, Darmstadt), Hyperforat™, Extract™ Z 90017, Neuroplant™, Neuropas™, Esbericum™, Remotiv™ (Bayer, Germany) and Sedaristan™. The following companies also produce St. John's Wort commercially: PhytoPharmica, Nature's Way, Herb Phyters, Enzymatic Therapy, Herbal Choice, Botalia Gold and Herb Pharm.

There is one commercially available hypericin product called VIMRxyn™ available from VIMRx Pharmaceuticals.

6.2 FRACTIONAL ANALYSIS ON A SILICA GEL COLUMN

In our studies, the fractionation of an alcoholic tinture of St. John's Wort was performed using normal phase column chromatography. This method was selected as a preferable pre-chromatographic technique on the basis of observed excellent mass recovery, the separation of the selected standards (flavonoids: mangiferin, rutin, hyperoside, quercitrin, quercitin; hypericin), as well as separation of other co-eluting components. A detailed description of the materials and methods utilized is presented below.

The chemical markers for St. John's Wort were chosen using the following procedure. A comprehensive search of the literature on St. John's Wort (*Hypericum perforatum*) indicated the hypericins, as well as some of the major flavonoids (rutin, quercetin, quercitrin), as the components with the most consistent bioactivity in a number of assays [flavonoids: analgesic, sedative, MAO activity; hypericin: antiviral (Bystrov, 1975), antidepressant & anxiolytic (Duke, 1992)]. These findings support the common uses in Europe for treating infections and depression. This was determined by different groups either by biotesting individual components or compound class enriched fractions, which contains the bulk of the hypericins and flavonoids.

Herb Materials: an alcoholic tincture of St. John's Wort (*Hypericum perforatum*) raw material was purchased from a commercial source.

The liquid extract (SJ041, 14 ml) was evaporated to dryness under vacuum, at low temperature and in the absence of light to yield 0.64 g of residue. The dried residue was triturated (intimately mixed) with four parts of Silica gel and carefully sifted on top of a glass column pre-packed with 30 g of Silica gel in chloroform. Development of the column over a six-hour period was accomplished by step gradient using chloroform: methanol. In the elution process, 200 ml of solvent volume was employed for each step, with the ratio being changed from 8:2, to 7:3, 1:1, and finally 100% methanol. Fractions 1 and 2, consisting of two distinctive colored bands, were obtained from the ratio 8:2 $CHCl_3$:MeOH eluent. The other fractions represent the eluates from each subsequent gradient elution. The collected fractions were evaporated to dryness under vacuum and their yield given below:

| eluent solvent (chloroform:methanol) | | fraction | weight |
|---|---|---|---|
| ratio | volume (ml) | No. | (mg) |
| 8:2 | 200 | SJ041-1 | 56.9 |
|  |  | SJ041-2 | 60 |
| 7:3 | 200 | SJ041-3 | 150.3 |

-continued

| eluent solvent (chloroform:methanol) | | fraction | weight |
|---|---|---|---|
| ratio | volume (ml) | No. | (mg) |
| 1:1 | 200 | SJ041-4 | 49.8 |
| methanol | 200 | SJ041-5 | 115.1 |

TLC Analysis:

The TLC chromatogram showed a text-book separation of the five fractions listed above. Reference standards of contained phytochemicals were not co-chromatographed. The chemical content of the fractional analysis is shown in FIG. 4.

4.1 g of Indena "0.3% hypericin" (Indena IDB, Milano, Italy) (SJ533-0) was adsorbed onto about 12 g of silica and eluted over 120 g of silica packed in chloroform. The column was eluted with a step gradient of $MeOH/CHCl_3$ (9:1, 8:2, 7:3, 6:4, 1:1, and washed with 100% MeOH followed by MeOH/HOAc 200:1). Ten fractions (SJ533-1 through SJ533-10) were collected to yield 4.4 g ((0.12, 0.03, 0.29, 0.48, 0.50, 0.47, 0.39, 0.04, 0.7, 1.38 g respectively).

Fractions SJ0533-9 (0.7 g) and SJ0533-10 (1.38 g), essentially the column wash material, were combined and relabeled as SJ 035533-910 or SJ-910. (1.3 g). This material was rechromatographed in a similar fashion over silica, using the same solvents and step gradient as above, to yield 34 fractions which were combined to produce nine fractions (SJ-910-1 through SJ-910-9) total yield 1.2 g. $GABA_A$ agonist activity results were reported as 50%, 100%, 55% and 80% for fractions SJ-910-6 through SJ-910-9 respectively.

Based on the above bioassay results, analysis focused on fraction SJ-910-7. This fraction totaled approximately 94 mg and represents 3.4% of the original extract. LC-MS investigation led to the discovery of a compound tentatively identified as a quinic acid acetate of molecular weight 234 amu. Further investigation revealed at least two additional, previously co-eluting, peaks of the same molecular weight. In order to obtain sufficient material for isolation and identification of active substance(s), investigations into scale up were begun.

SJ-910-8 and SJ-910-9 from above (approx 900 mg) were also separated or chromatographed on an HP-20 column as described below to yield 5 fractions.

Scale-up fractionation:

Indena "0.3% hypericin" was used in its entirety (1 kg) for scale up purposes. A small portion of this material was chromatographed on a Dianon column (HP-20) and eluted stepwise with water, 20% MeOH, 50% MeOH, 50–100% MeOH, 100% MeOH and MeOH—$CHCl_3$, to obtain six fractions. $GABA_A$ agonist activity was highest for fractions 3–5 of this scale up trial.

The bulk of the kilogram of sample #035531 was repeatedly absorbed on silica and eluted stepwise in a similar system to that used in the two previous column separations ($MeOH/CHCl_3$ 8:2, 7:3, 1:1, 100% MeOH, MeOH/HOAc; the $MeOH/CHCl_3$ 9:1 step was deleted) producing 5 fractions. The 100% MeOH and MeOH/HOAc fractions (4 and 5) were combined, evaporated to approx. 260 g of syrup, dissolved in water and subjected to the HP-20 column separation described above to produce 7 fractions. These fractions were labeled as follows: SJ2HP-W (water), SJ2HP-20M (20% MeOH), SJ2HP-40M (40% MeOH), SJ2HP-50M (50% MeOH, three fraction were initially collected and later combined), SJ2HP-M-1 (100% MeOH), SJ2HP-M-2 (100% MeOH), and SJ2HP-M-C.

6.3 BIOLOGICAL ACTIVITY ANALYSIS MONOAMINE OXIDASE, SEROTONIN TRANSPORTER ASSAY, OTHER ASSAYS

6.3.1 BIOASSAY FOR GABA$_A$ BINDING

The GABA$_A$ binding activity assay with St. John's Wort extracts and fractions can be performed using techniques standard in the art (e.g. Enna et al., 1977, Brain Research. 124: 185–190; Falch et al., 1986 J. Neurochem. 47(3):898–903). The reference literature compounds for this assay include diazepam and muscimol (Sigma Chemical Company).

By way of example, but not of limitation, the GABA$_A$, agonist site binding assay is performed as briefly described below.

Using receptors derived from bovine cerebellar membranes, a [$^3$H]-GABA (70–90 Ci/mmol) radioligand with a final concentration of 5.0 nM, and GABA are mixed and incubated in 50 mM TRIS-HCl (pH 7.4) at 0–4° C. for 60 minutes. The reaction is terminated by rapid vacuum filtration onto glass fiber filters. Radioactivity trapped onto the filters is determined and compared to control values in order to ascertain any interactions of test compound with the GABA$_A$ receptor.

| Reference Compounds | Ki(nM) |
|---|---|
| Muscimol | 4.4 |
| Isoguvacine | 9.5 |
| GABA | 23.1 |
| THIP* | 25.1 |

Assay Characteristics:

K$_D$ (binding affinity): 370 nM
B$_{max}$ (receptor number): 0.7 pmol/mg protein

*THIP 4,5,6,7-Tetrahydroisoxazolo[5,4-c]pyridin3(2H)-one).

6.3.2 BIOASSAY FOR NMDA AGONIST SITE BINDING

The glutamate NMDA agonist site binding assay with St. John's Wort extracts and fractions is conducted using techniques standard in the art (e.g. Lehmann et al., 1988, J. Pharmac. Exp. Ther. 246:66–75; Murphy et al., 1987, J. Pharmac. Exp. Ther. 240: 778–784).

By way of example, but not of limitation, the glutamate, NMDA agonist site binding, assay is performed as briefly described below.

Using receptors derived from rat forebrain membranes, a [$^3$H]-CGP 39653 (25–60 Ci/mmol) radioligand with a final concentration of 2.0 nM, and NMDA are mixed and incubated in 50 mM TRIS-Acetate (pH 7.4) at 0–4° C. for 60 minutes. The reaction is terminated by rapid vacuum filtration onto glass fiber filters. Radioactivity trapped onto the filter is determined and compared to control values in order to ascertain any interactions of test compound with the NMDA binding sites.

| Reference Compounds | Ki(nM) |
|---|---|
| NMDA | 9,300 |

Assay Characteristics:

K$_D$ (binding affinity): 7.0 nM
B$_{max}$ (receptor number): 0.77 pmol/mg tissue

6.3.3 BIOASSAY FOR M$_1$ BINDING

The muscarinic M$_1$ binding assay with St. John's Wort extracts and fractions is done using techniques standard in the art (e.g. Watson et al., 1983, Life Sciences. 32:3001–3011; Luthin and Wolfe, 1984, Molec. Pharmac. 26:164–169).

By way of example, but not of limitation, the muscarinic, M$_1$ binding, assay is performed as briefly described below.

Using receptors derived from bovine striatal membranes, a [$^3$H]-Pirenzepine (70–87 Ci/mmol) radioligand with a final concentration of 1.0 nM, and atropine are mixed and incubated in 25 mM HEPES (pH 7.4) at 25° C. for 60 minutes. The reaction is terminated by rapid vacuum filtration onto glass fiber filters. Radioactivity trapped onto the filters is determined and compared to control values in order to ascertain any interactions of test compound with the muscarinic binding site.

| Reference Compounds | Ki(nM) |
|---|---|
| Atropine | 0.4 |
| Pirenzepine | 4.5 |
| Telenzepine | 64.5 |

Assay Characteristics:

K$_D$ (binding affinity): 2.2 nM
B$_{max}$ (receptor number): 1.4 pmol/mg protein

6.3.4 MONOAMINE OXIDASE-A (MAO$_A$)

Monoamine oxidase (MAO, E.C.1.4.3.4) is an enzyme of broad specificity in that it catalyzes the removal of an amine group from a variety of substrates, including endogenous substances (norepinephrine, epinephrine, dopamine, tyramine, 5-hydroxytryptamine) and many drugs that are amines. MAO functions as an important protective mechanism against exogenous, biologically active amines. There are at least two types of MAO, which display dissimilar preferences for substrates and differential sensitivities to selective inhibitors; these were originally defined by sensitivity to clorgyline and preference for 5-HT (MAO$_A$), and sensitivity to selegiline (deprenyl) and preference for phenylethylamine (MAO-B). The two types of MAO appear to be distinct molecular entities that exist in various proportions in different tissues. The MAO inhibitors currently in therapeutic use are relatively nonselective, but selective inhibitors may offer advantages in certain clinical settings. Only selective inhibitors of MAO$_A$ (e.g. clorgyline) appear to have efficacy in the treatment of major depression, and a selective MAO-B inhibitor may have a beneficial effect on Parkinson's disease and dyskinesia.

MAO$_A$ enzyme activity is assayed in a mitochondrial fraction isolated from rat brain by differential centrifugation.

40 μg of membrane protein in 20 mM phosphate buffer (pH 7.4) is mixed with test compound (at 10 μM), and the reaction is started by the addition of 95 μM [$^3$H]-serotonin (2–10 mCi/mmol). Following 20 minutes incubation at 37° C., the reaction is terminated by the addition of 5% HCl. The radioactivity of [$^3$H]-serotonin in an extraction is determined. Compounds are screened at 10 μM. (Medvedev et al., 1994, *Biochem. Pharmacol.* 47: 303–308).

| Inhibition of Monoamine Oxidase A Activity | |
|---|---|
| Compound | IC$_{50}$ (μM) |
| Tetrindole Mesylate | 0.046 |
| Pirlindole Mesylate | 0.016 |
| *Clorgyline | 0.00089 |

*Standard reference compound

The results of the monoaminooxidase A assay are described in the summary tables below.

6.3.5 MONOAMINE OXIDASE B

MAO-$_B$ enzyme activity is assayed in a mitochondrial fraction isolated from rat liver by differential centrifugation. 40 μg of membrane protein in 20 mM phosphate buffer (pH 7.4) is mixed with test compound (at 10 μM), and the reaction is started by the addition of 140 μM [$^3$H]dopamine (2–10 mCi/mmol). Following 20 minutes incubation at 37° C., the reaction is terminated by the addition of 5% HCl. The radioactivity of [$^3$H]dopamine in an extraction was determined. (Egashira et al. 1976, *Biochem. Pharmacol.* 25: 2583–2586).

The following reference compounds are used for the inhibition of monoamine oxidase B: reference compounds, (IC$_{50}$ (μM)); N-(2-aminoethyl)-4-chlorobenzamide hydrochloride, (23); N-(2-aminoethyl)-3-iodobenzamide hydrochloride, (1.7); and clorgyline, (0.0027).

6.3.6 SEROTONIN TRANSPORTER ASSAY

This assay measures binding of [$^{125}$I]-RTI-121 to presynaptic sites associated with the uptake of serotonin. Cerebral cortical membranes derived from male Wistar rats, weighing 175±25 g are prepared in modified Tris-HCl pH 7.4 buffer using standard techniques. A 5 mg aliquot of membrane is incubated with 10 pM [$^{125}$I]-RTI-121 for 90 minutes at 25° C. Non-specific binding is estimated in the presence of 100 μM clomipramine. Membranes are filtered and washed 3 times and the filters are counted to determine [$^{125}$I]-RTI-121 specifically bound. Compounds are screened at 10 μM (Boja et al. 1992, *Synapse* 12:27–36).

| Assay Reference Data: Kd 1.1 nM | | | |
|---|---|---|---|
| Bmax: 322 fmol/mg protein | | | |
| Specific Binding: 85% | | | |
| Reference Data: | | | |
| Compound | IC$_{50}$ (nM) | Ki (nM) | nH |
| Clomipramine | 1,100 | 1,100 | 0.5 |
| Quipazine maleate | 560 | 550 | 0.8 |
| 6-NO-Quipazine | 3,400 | 3,400 | 0.7 |
| Trazodone | 5,500 | 5,400 | 0.8 |
| Mianserin | 6.4 | 2.1 | 1.0 |

Fourteen additional bioassays were preformed on either extracts, fractions or reference compounds for this botanical.

To measure inhibition of [$^3$H] PK11195 to the benzodiazepine receptor (BDZ) a partially purified receptor preparation was made from rat kidney membranes. The final radioactive ligand concentration was 1 nM and non-specific binding was measured using 200 nM cold PK11195. The substances, receptor and ligand were reacted in 50 mM Tris-HCL (pH 7.7) at 0–4° C. for 60 minutes. The reaction was terminated by rapid filtration of the samples through glass fiber filters. The amount of specific activity was determined by liquid scintillation counting (Skowronski, R et al. *Eur. J. Pharmacology* 148: 187–193, 1988). The inhibition of [$^3$H] pinrenzepine to the muscarinic M1 receptor (M1) by the substances was measured using a partially purified receptor from bovine striatal membranes. The final hot ligand concentration was 1 nM and non-specific binding was determined in the presence of 100 nM atropine. The reactions were carried out in 25 nM HEPES (pH 7.4) at 25° C. for 60 minutes. The reactions were terminated by rapid vacuum filtration of the reaction mixture through glass fiber filters. Bound radioactivity was determined by liquid scintillation counting Watson et al. *Life Sciences* 32: 3001–3011, 1983). To assay for biological activity for the muscarinic receptor for the central nervous system, receptor was partially purified from rat cortical membranes. The radioligand used was [$^3$H] quinuclidinylbenzilate (QNB) at a final ligand concentration of 0.15 nM. Non-specific binding was determined in the presence of 100 nM atropine. The assay reactions were carried out in 50 mM Tris-HCl (pH 7.4) for 60 minutes at 25° C. The reactions were terminated by rapid vacuum filtration of the reaction mixture through glass fiber filters (Luthin, G. R. and Wolf, B. B. *J. Pharmac. Exp. Ther* 228: 648–655, 1984). To assay for activity for the glutamate receptor two assays were performed. In the first assay the agonist site of the glutamate receptor was studied (NMDA). Here, the receptor was a partially purified material made from rat forebrains. The radioligand was [$^3$H] CGP 39653 at a final ligand concentration of 2 nM. Non-specific binding was determined using 1 mM NMDA. The assay reactions were carried out in 50 nM Tris-acetate (pH 7.4) at 0–4° C. for 60 minutes. The reactions were terminated by rapid vacuum filtration of the reaction mixture through glass fiber filters (Lehmann, J. et al. *J. Pharmac. Exp. Ther.* 246: 65–75, 1988). In the second assay for the glutamate receptor the reactions were carried out using [$^3$H] AMPA at a final concentration of 5 nM. Non-specific binding was determined using 100 μM AMPA. The assay reactions were carried out in 10 mM K$_2$HPO$_4$/100 mM KSCN (pH 7.5) at 0–4° C. for 60 minutes. The reactions were terminated by rapid vacuum filtration of the reaction mixture through glass fiber filters (Murphy et al. *Neurochem. Res.* 12: 775–781, 1987). To measure the inhibition of the cholecystokinin receptor of the central nervous system (CCK$_B$) a partially purified receptor preparation from mouse forebrain membranes was prepared. A final concentration of [$^{125}$I] cholecystokinin at 0.02 nM was used and non-specific binding was determined in the presence of 1 μM of sulfated cholecystokinin 8. The reactions of the substances and the ligands were carried out in 20 mM HEPES containing 360 mM NaCl, 15 mM KCl, 5 mM MgCl2, 1 mM EGTA and 0.25 mg/ml of bacitracin (pH 6.5) at 25° C. for 120 minutes. The reactions were terminated by rapid vacuum filtration of the reaction mixture through glass fiber filters (Wennogle, L. et al. *Life Sciences* 36: 1485–1492, 1985).

The inhibition of MAO$_A$ enzymatic activity (MAO$_A$) was determined using rat liver mitochondrial membranes as a partially purified enzyme source. The substrate was [$^{14}$C] serotonin and non-specific activity was determined using 1

μM of Ro 41-1049. The reaction involves the conversion of the substrate to [$^{14}$C] 5-hydroxyl indoleacetaldehyde+$NH_4^+$. In brief, the enzyme is preincubated with the substances and the subtype specific blocker deprenyl (at 300 nM) for 60 minutes at 37° C. in 100 mM $KPO_4$ (pH 7.2). Substrate is added and incubated for an additional 10 minutes. The reaction is terminated by the addition of 0.5 ml of 2M citric acid. Radioactive product is extracted into a toluene/ethyl acetate fluor and compared to control samples using scintillation spectrophotometry (Otsuka, S. and Kobayashi, Y. *Biochem. Pharmacol.* 13: 995–1006, 1964). Nitric oxide synthetase activity was measured using a binding assay (NOS). The receptors were made by partial purification of material from rat brain membranes. The radioligand used was [$^3$H] L-$N^G$-Nitro-Arginine (NOARG) at a final concentration of 5 nM. Non-specific binding was determined using 100 μM of NOARG. The assay reactions were carried out in 50 mM Tris-HCl (pH 7.4) for 60 minutes at 25° C. The reactions were terminated by rapid vacuum filtration of the reaction mixture through glass fiber filters (Michel, A. D. et al. *Brit. J. Pharmacology* 109: 287–288, 1993).

To determine the inhibitory activity of the substances for the dopamine receptor (dp) the following assay was preformed. A partial receptor preparation was prepared from bovine striatal membranes using [$^3$H] spiperone as the ligand at a final concentration of 0.3 nM. To determine non-specific binding cold spiperone was tested at 1 μM. The reactions were carried out in 50 mM Tris-HCl (pH 7.7) containing 120 mM NaCl, 5 mM KCl, 2 mM $CaCl_2$ and 1 mM $MgCl_2$ at 37° C. for 60 minutes. The reactions were terminated by rapid vacuum filtration of the reaction mixture through glass fiber filters (Leysen et al. *Biochem. Pharmacol.* 27: 307–316, 1978). The inhibitory properties of the substances for binding of ligand to the adenosine receptor (ADNS) was measured using a partially purified receptor preparation made from bovine striatal membranes. The radioligand used was [$^3$H] 5'-N-ethylcarboxyamidoadenosine (NECA) at a final ligand concentration of 4 nM. Non-specific binding was determined in the presence of 10 μM NECA. The reactions were carried out in 50 mM Tris-HCL (pH 7.7) for 60 minutes at 25° C. The reactions were terminated by rapid vacuum filtration of the reaction mixture through glass fiber filters (Bruns, R. et al. *Pharmacology* 29: 331–346, 1986). To measure the inhibitory activity of the substances for the opiate receptor (Opiate) receptor was partially purified from rat forebrains. [$^3$H] naloxone at 1 nM as the ligand used. Non-specific binding was determined in the presence of 1 μM of naloxone. The assays were carried out in 50 mM Tris-HCl (pH 7.4) at 25° C. for 90 minutes. The reactions were terminated by rapid vacuum filtration of the reaction mixture through glass fiber filters (Pert, C. and Snyder, S. H. *Mol. Pharmacology* 19: 868–879, 1974). The neuronal nicotinic receptor (Nicotinic Neuronal) was assayed using receptors partially purified from rat cortical membranes. The radioligand used was [$^3$H] N-methylcarbamylcholine iodide at a final ligand concentration of 5 nM. Non-specific binding was determined in the presence of 1 μM nicotine sulfate. The assay reactions were carried out in 50 mM Tris-HCl (pH 7.4) containing 120 mM NaCl, 5 mM KCl, 2 mM $CaCl_2$, 1 mM $MgCl_2$, and 3 μM atropine sulfate at 4° C. for 60 minutes. The reactions were terminated by rapid vacuum filtration of the reaction mixture through glass fiber filters (Boska, P. and Quirion, R. *Eur. J. Pharmacology* 139: 323–333, 1987). To determine how the substances inhibit the corticotropin releasing factor (CRF) partially purified receptor from rat cortical membranes was used as the receptor preparation. The radioligand used was [$^{125}$I] Tyr-° CRF at a final ligand concentration of 0.1 nM. Non-specific binding was determined in the presence of 1 μM Tyr-° CRF. The reactions were carried out in 50 mM HEPES containing 10 mM $MgCl_2$, 2 mM EGTA, 0.12 TIU/ml aprotinin and 0.3% BSA at 25° C. for 120 minutes. The reaction is terminated by centrifugation in a Sorvall centrifuge for 15 minutes at 4° C. After repeated washings the resulting pellet is dissolved and radioactivity is measured using a gamma counter (De Souza, E. B. *J. Neuroscience* 7: 88–100, 1987).

The inhibitory activity of the substances for the endothelin receptor (Endothelin) were tested using a human recombinant receptor expressed in CHO cells. The radioligand used was [$^{125}$I] endothelin at a final ligand concentration of 0.03 nM. A 1 μM concentration of cold endothelin was used to determine non-specific binding. The assay reactions were carried out in 50 mM Tris-HCl (pH 7.4) containing 0.5 mM $CaCl_2$, 0.05% Tween-20 and 0.1% BSA at 25° C. for 90 minutes. The reactions were terminated by rapid vacuum filtration of the reaction mixture through glass fiber filters (Bolger, G. T. et al. *J. Cardiovascular Pharmacology* 16: 367–375, 1990).

Through an NIMH screening contract (NovaScreen™, Baltimore, Md.) a commercially available crude extract from the fresh flowers and buds of *Hypericum perforatum* [1:1.5; hydro-alcohol (40:60) made from flowering tops; Herb Pharm] containing ~0.1% hypericin was dried under vacuum, dissolved in 4% DMSO, and diluted to an initial concentration of 50 mg/ml for in vitro screening in a battery of 39 receptor assays and two enzyme systems (Table 5, below). The receptor assays showing at least 50% displacement of radioligand (or 50% inhibition of MAO) were considered "hits."

TABLE 5

Screen Receptor Binding/Enzyme Activity Assays Performed with St. John's Wort Extract

| | |
|---|---|
| Adrenergic ($X_{1,2}$, β) | Glycine (strychnine) |
| Dopamine ($DA_{1,2}$) | $GABA_A$ |
| Serotonin ($5HT_{1,2}$) | $GABA_B$ |
| Quisqualate | NMDA |
| Kainate | Adenosine (non-selective) |
| Angiotensin II | Arg-Vasopressin 1 |
| Bombesin | $GABA_A$ |
| Substance P | $GABA_B$ |
| Substance K | NMDA |
| Neurotensin | Adenosine (non-selective) |
| Neuropeptide Y | Glycine (strychnine) |
| Somatostatin | $GABA_A$ |
| Forksolin | Calcium (N, T, L) |
| Phorbol Ester | Chloride |
| Inositol triphosphate ($IP_3$) | Potassium |
| Glycine (non-strychnine) | |
| MK-801 | $MAO_A$ |
| PCP | $MAO_B$ |
| Benzodazepine (central BDZ) | |

Concentration-response curves ($IC_{50}$) were then performed for the "hits." Receptor assays showing at least 50% displacement of radioligand (or 50% inhibition of MAO) were considered hits. The results are shown in table 6, below.

The crude extract of St. John's Wort had significant receptor affinity for adenosine, $GABA_A$, $GABA_B$, benzodiazepine, inositol triphosphate ($IP_3$,) and monoamine oxidase ($MAO_A$, MAO-B). The inhibition of MAO by crude St. John's Wort extracts is consistent with previous reports (Bladt and Wagner, 1994; Suzuki et al., 1984, *Planta Medica.* 50:272–274; Thiede and Walper, 1994).

TABLE 6

Screening Assay "Hits"

| Extract Concentration | % Inhibition in Various Assays | | | | | | | |
|---|---|---|---|---|---|---|---|---|
| [μg/ml] | Adenosine | $GABA_A$ | $GABA_B$ | $5HT_1$ | BDZ | $IP_3$ | $MAO_A$ | $MAO_B$ |
| 0.005 | -2 | 7 | 45 | 12 | -4 | -3 | 9 | -1 |
| 0.05 | 13 | 43 | 85 | 12 | 0 | 16 | 4 | -10 |
| 0.5 | 17 | 94 | 105 | 9 | 0 | 13 | 33 | -2 |
| 5.0 | 20 | 100 | 109 | 12 | 19 | 40 | 97 | 53 |
| 50 | 71 | 101 | 114 | 54 | 65 | 107 | | |
| ~$K_I$ (μg/ml)* | 1 | 0.075 | 0.006 | 25 | 24 | 10 | 2 | 3.2 |

*$K_i = IC_{50}/1$ + ligand affinity/ligand concentration

Unlike the crude extract, however, synthetic hypericin (95%) lacked significant $MAO_A$ or $MAO^B$ inhibition at concentrations up to 0.1 mM (Table 7). Hypericin had affinity only for NMDA receptors ($K_i$~1M) and this may play a role in its reported antiviral activity since NMDA antagonists prevent gp 120-induced neurotoxicity (Diop et al., 1994, *Neuroscience Letters* 165:187–190).

TABLE 7

Receptor Binding/Enzyme Inhibition by Hypericin

| Drug conc. (μM) | % Inhibition $MAO_A$ | $MAO^B$ | NMDA |
|---|---|---|---|
| .001 | — | — | 10.5 |
| .01 | — | — | 24.5 |
| .1 | — | — | -0.3 |
| 1 | — | — | 48.5 |
| 10 | 27.0 | -2.0 | 81.7 |
| 100 | 20.8 | -20.7 | |
| ~$K_i$ | — | — | 1.1 |

These data are consistent with recent pharmacologic evidence suggesting that other constituents of this plant may be more important than hypericin for the reported psychotherapeutic activity. Some of these results have been reported previously (Cott, 1995, *Psychopharm. Bulletin* 31:131–137; Cott, 1996, *Psychopharm. Bulletin* 31:745–751). With the exception of $GABA_A$ and $GABA_B$, the concentrations of St. John's Wort extract required for these in vitro activities may not be attained after oral administration in whole animals or humans. It is conceivable that the very high affinity of St. John's Wort extract for GABA receptors presented here may be important. Unless the responsible components are metabolized before they enter the general circulation, plasma levels sufficient to bind GABA receptors would be predicted. It should be noted that Müller, et al., (1996) reported an $IC_{50}$ of 3 μg/ml for $GABA_A$. The reason for this difference with the present finding is unknown.

The significance of this GABA binding is unknown at the present, but there is considerable literature on the role of GABA in affective disorders. $GABA_B$ stimulation has been found to enhance receptor down regulation during imipramine treatment (Enna, et al., 1986, in Bartholini et al. eds. *GABA and Mood Disorders: Experimental and Clinical Research*: Raven Press: New York, N.Y., 1986:23–49). Nielsen, et al. have reported antidepressant effects with the GABA-ergic agent, fengabine, in depressed outpatients (Nielsen et al. 1990, *Acta Psychiatrica Scandinavica* 82:366–371). Petty et al. have reported that GABA plasma levels are low in both bipolar and unipolar depression, and that benzodiazepines (which enhance $GABA_A$ activity) may be effective antidepressants as well as anxiolytics (Petty et al., 1992, *Biological Psychiatry* 32:354–363; Petty et al., 1993, *Neuropsychopharmacology* 9:125–132; Petty et al., 1995, *Biological Psychiatry* 38:578–591). GABA neuronal systems also modulate dopamine and dopamine-induced behaviors (Cott, et al., 1976, *Naunyn Schmiedebergs Arch. Pharmacol.* 295:203–209; Cott and Engel, 1977, *J. Neural Transm.* 40:253–268).

6.3.7 SUMMARY OF BIOASSAYS

The results for the bioassays are presented in the summary Tables 8 and 9A–9I below. See the individual bioassays for the experimental details above.

TABLE 8

St. John's Wort Extract-Biological Assays

| Standard/Extract/Fraction | $MAO_A$ | 5-HT Reuptake |
|---|---|---|
| Extract #1 | Negative | Negative |
| Extract #2 | Negative | Negative |
| Fraction 1 | Negative | Negative |
| Fraction 2 | Negative | Negative |
| Fraction 3 | Negative | Negative |
| Fraction 4 | Negative | Negative |
| Fraction 5 | Negative | Negative |
| Hypericin | Negative | 4 μM |
| Hyperoside | Negative | Negative |
| Rutin | Negative | Negative |
| Quercetin | 1.9 μM | Negative |
| Quecetrin | Negative | Negative |
| Magniferin | Negative | Negative |

The biological assays verified the $MAO_A$ activity of quercetin and the serotonin uptake activity of hypericin. However, in these prehearing results neither the extracts (FIG. 4) nor the fractions (FIG. 5) contained sufficient quantities of either standard (quercetin, hypericin) to detect the two bioactivities. Therefore it was not possible to calculate the percent contribution of each of these components.

TABLE 9A

| Extracts ($10^{-4}$) | $GABA_A(10^{-4})$ | $BDZ(10^{-4})$ | $M_1(10^{-4})$ | Agonist NMDA ($10^{-4}$) |
|---|---|---|---|---|
| SJ053 | 88 | 43 | 48 | 39 |
| SJ054 | 97 | 24 | 36 | 46 |
| SJ055 | 94 | 25 | 60 | 40 |
| SJ056 | 95 | 25* | 39 | 37 |
| SJ057 | 93 | 39 | 61 | 22 |

TABLE 9A-continued

| | | | | |
|---|---|---|---|---|
| SJ058 | 93 | 42 | 42 | 44 |
| SJ060 | 94 | — | — | — |
| SJ041 | 100 | — | — | — |

| Fractions @ ($10^{-4}$) | $GABA_A(10^{-4})$ | $BDZ(10^{-4})$ | $M_1(10^{-4})$ | $NMDA(10^{-4})$ |
|---|---|---|---|---|
| SJ 533-1 | — | — | — | 46 |
| SJ 533-2 | — | 31 | — | — |
| SJ 533-3 | — | 64 | — | — |
| SJ 533-4 | — | 52 | — | — |
| SJ 533-5 | — | 27 | — | — |
| SJ 533-6 | — | 31 | — | — |
| SJ 533-7 | 38 | — | 21 | — |
| SJ-533-8 | 31 | — | — | — |
| SJ 533-9 | 100 | — | — | — |
| SJ 533-10* | 100 | — | — | 35 |

TABLE 9B

| Fractions - III | $GABA_A$ ($10^{-4}$) |
|---|---|
| SJ2HP-W | 95 |
| SJ2HP-20M | 45 |
| SJ2HP-40M | 45 |
| SJ2HP-50M | 62 |
| SJ2HP-M-1 | 37 |
| SJ2HP-M-2 | 67 |
| SJ2HP-M-C | 32 |
| 8139-0087 | 35 |
| 8139-0088 | 38 |
| 8139-0089 | 75 |
| 8139-0090 | 65 |
| 8139-0091 | 58 |
| 8139-0092 | 33 |

TABLE 9C

| | $CCK_B$ | $MAO_A$ | $MAO_B$ | Dp |
|---|---|---|---|---|
| Extracts ($10^{-4}$) | | | | |
| SJ053 | 49 | — | — | — |
| SJ054 | 47 | 24 | — | 22 |
| SJ055 | 52 | — | — | — |
| SJ056 | 44 | 26 | — | — |
| SJ057 | 30 | — | — | — |
| SJ058 | 44 | 25 | 25 | 35 |
| SJ060 | — | — | — | — |
| SJ041 | — | — | — | — |
| Fractions @ ($10^{-4}$) | | | | |
| SJ 533-1 | 78 | 42 | 30 | 67 |
| SJ 533-2 | 43 | 41 | — | 40 |
| SJ 533-3 | 32 | 30 | — | — |
| SJ 533-4 | — | — | — | — |
| SJ 533-5 | — | 20 | — | — |
| SJ 533-6 | — | — | — | — |
| SJ 533-7 | — | — | — | — |
| SJ-533-8 | — | — | — | — |
| SJ 533-9 | 35 | — | — | — |
| SJ 533-10* | — | — | — | — |

TABLE 9D

| | Sero | ADNS | Glut AMPA | $M_1$ Central | Opiate NS |
|---|---|---|---|---|---|
| Extracts ($10^{-4}$) | | | | | |
| SJ053 | — | 46 | 24* | 29* | 24* |
| SJ054 | — | 27 | 25 | — | — |
| SJ055 | — | 26 | 20 | — | — |
| SJ056 | 819 μM | 26 | 27 | 28 | 20 |
| SJ057 | — | — | — | 23 | — |
| SJ058 | — | 25 | 25 | 25 | 20 |
| SJ060 | — | — | — | — | — |
| SJ041 | — | — | — | — | — |
| Fractions @ ($10^{-4}$) | | | | | |
| SJ 533-1 | — | 39 | — | — | 66 |
| SJ 533-2 | — | 23 | — | — | 39 |
| SJ 533-3 | — | — | — | — | 24 |
| SJ 533-4 | — | — | — | — | — |
| SJ 533-5 | — | 35 | — | — | — |
| SJ 533-6 | — | 29 | — | — | — |
| SJ 533-7 | — | 28 | — | — | — |
| SJ-533-8 | — | — | — | — | — |
| SJ 533-9 | — | — | — | — | — |
| SJ 533-10* | — | — | — | — | — |

TABLE 9E

| Extracts ($10^{-4}$) | NOS | Endothelin | Opiate NS | Nicotinic Neuronal | CRF |
|---|---|---|---|---|---|
| SJ053 | 32 | 31* | — | — | — |
| SJ054 | 25 | — | — | — | — |
| SJ055 | 25 | — | — | — | — |
| SJ056 | 36 | 37 | — | 31 | — |
| SJ057 | 21 | 37 | — | 21 | 32 |
| SJ058 | 38 | 40 | — | — | — |
| SJ060 | — | — | — | — | — |
| SJ041 | — | — | — | — | — |

TABLE 9F

| Extracts ($10^{-4}$) | $GABA_A(10^{-4})$ | $BDZ(10^{-4})$ | $M_1(10^{-4})$ | Agonist $NMDA(10^{-4})$ |
|---|---|---|---|---|
| Hypericin | 31 | 33 | 80 | — |
| Quercetin | — | — | — | — |
| Amentoflavone | — | — | — | NT |
| Quercitrin | — | — | — | — |
| Hyperoside | — | — | — | — |
| Mangiferin | — | — | — | — |
| Rutin | — | — | — | — |
| Caffeic acid | — | — | — | NT |
| Chlorogenic acid | — | — | — | NT |
| Catechin | — | — | — | NT |
| Epidatechin | — | — | — | NT |
| p-Coumaric acid | — | — | — | NT |
| Ferulic acid | — | — | — | NT |
| Iso-Ferulic acid | — | — | — | NT |
| Acetiquinic acid | — | — | — | NT |
| Quinic acid | — | — | — | NT |

TABLE 9G

| Extracts (10⁻⁴) | CCK_B | MAO_A | MAO_B | dp |
|---|---|---|---|---|
| Hypericin | — | — | — | — |
| Quercetin | — | 8.2 μM | 2.4 μM | — |
| Amentoflavone | NT | — | — | NT |
| Quercitrin | — | — | — | — |
| Hyperoside | — | — | — | — |
| Mangiferin | — | — | — | — |
| Rutin | — | — | — | — |
| Caffeic acid | NT | — | — | NT |
| Chlorogenic acid | NT | — | — | NT |
| Catechin | NT | — | — | NT |
| Epidatechin | NT | — | — | NT |
| p-Coumaric acid | NT | — | — | NT |
| Ferulic acid | NT | — | — | NT |
| Iso-Ferulic acid | NT | — | — | NT |
| Acetiquinic acid | NT | — | — | NT |
| Quinic acid | NT | — | — | NT |

TABLE 9H

| Extracts (10⁻⁴) | Sero | ADNS | Glut AMPA | M₁ Central | Opiate NS |
|---|---|---|---|---|---|
| Hypericin | 4 μM/51 | 70 | — | 55 | 43/87 |
| Quercetin | — | 45/27 | — | 27 | — |
| Amentoflavone | — | — | — | — | — |
| Quercitrin | 39 | 45 | — | — | — |
| Hyperoside | — | — | — | — | — |
| Mangiferin | — | — | — | — | — |
| Rutin | — | — | — | — | — |
| Caffeic acid | — | — | — | — | — |
| Chlorogenic acid | — | — | — | — | — |
| Catechin | — | — | — | — | — |
| Epidatechin | — | — | — | — | — |
| p-Coumaric acid | — | — | — | — | — |
| Ferulic acid | — | — | — | — | — |
| Iso-Ferulic acid | — | — | — | — | — |
| Acetiquinic acid | — | — | — | — | — |
| Quinic acid | — | — | — | — | — |

TABLE 9I

| Extracts (10⁻⁴) | NOS | Endothelin | OPNS | Nicotinic Neuronal | CRF |
|---|---|---|---|---|---|
| Hypericin | 48 | — | 44 | — | — |
| Quercetin | — | — | — | — | — |
| Amentoflavone | — | NT | — | NT | NT |
| Quercitrin | — | — | — | — | — |
| Hyperoside | — | — | — | — | — |
| Mangiferin | — | — | — | — | — |
| Rutin | — | — | — | — | — |
| Caffeic acid | — | NT | — | NT | NT |
| Chlorogenic acid | — | NT | — | NT | NT |
| Catechin | — | NT | — | NT | NT |
| Epidatechin | — | NT | — | NT | NT |
| p-Coumaric acid | — | NT | — | NT | NT |
| Ferulic acid | — | NT | — | NT | NT |
| Iso-Ferulic acid | — | NT | — | NT | NT |
| Acetiquinic acid | — | NT | — | NT | NT |
| Quinic acid | — | NT | — | NT | NT |

Bioassay Data summary of column fractions SJ5331-10

The starting material, SJ533-0 (Indena extract powder, see Section 6.4 above for details of fractionation) was active for GABA_A agonist activity (100% at 1.0E-4). The only fractions to match this activity were SJ533-9 and SJ533-10.

The following activities were also reported: SJ533-1, Non selective opiate and CCK_B cholecytokinin; SJ533-3 and SJ533-4, GABA_A central benzodiazepine.

GABA_A agonist activity for column fractions SJ910-1-10 at 1.0E-4

This column was a sub fractionation of SJ533-9 and SJ533-10 above. The original material (the material before this sub fractionation) was not tested.

| SJ910 frac. | 1 | 2 | 3 | 4 | 5 | 6 | 7 | 8 | 9 |
|---|---|---|---|---|---|---|---|---|---|
| % result | 33 | 26 | 26 | −5 | −10 | 49 | 100 | 55 | 80 |

6.4 ACTIVE COMPONENTS OF ST. JOHN'S WORT IN THE LITERATURE

St. John's Wort contains numerous compounds with documented biological activity. Most researchers consider its effects to be due to a variety of constituents rather than any single component. Constituents that have stimulated the most interest include the naphthodianthrones, hypericin and pseudohypericin and a broad range of flavonoids including quercetin, quercitrin, amentoflavone and hyperin. Both the napththodianthrones and the flavonoid classes of compounds are reported to contribute to its antidepressant and antiviral activity. The phloroglucinols, hyperforin and adhyperforin, the essential oil, flavonoids and xanthones all contribute to St. John's Wort's wound-healing properties.

6.4.1 ST. JOHN'S WORT COMPONENTS

The major reported naphthodianthrone derivatives of St. John's Wort are naphthodianthrone derivatives (<0.1–0.15%) (*Deutscher Arzneimittel-Codex.* 3rd Supplement 91 ed. 1986); hypericin [0.02–1.8%] (Benigni et al., *Hypericum, Piante Medicinali: Chimica, Farmacologia e Terapia.* Inverni & Della Beffa, Milano, 1971.), pseudohypericin, isohypericin, emodin-anthrone. In fresh material protohypericin and protopseudohypericin are also present. These biosynthetic precursors are transformed into hypericin and pseudohypericin by exposure to light. Cyclopseudohypericin is also cited and is an oxidation product of pseudohypericin (ESCOP, 1996, Monograph St. John's wort. European Scientific Cooperative for Phytomedicines).

6.4.2 HYPERICIN CONTENT OF ST. JOHN'S WORT

The highest concentrations of hypericin have been observed in the dried flowers (Benigni, 1971) followed by the capsules and uppermost leaves (Benigni, 1971; Southwell and Campbell, 1991, *Phytochemistry* 30:475–478). Narrow-leafed varieties which have a relatively high number of oil glands [6.2 per mm] are reported to yield significantly higher concentrations of hypericin than broad-leafed varieties [2.2 oil glands per mm] (Southwell and Campbell, 1991).

| Hypericin content in various parts of *H. perforatum* in g % | |
| --- | --- |
| Young plant (12 cm tall) | 0.027 |
| Whole plant w/flowers | 0.036–0.2 |
| Whole plant w/buds | 0.042 |
| Dried flowers | 0.196–1.8 |
| Fresh flowers | 0.09–0.12 |
| Petals | 0.245 |
| Leaves (average) | 0.019 |
| Stem | 0.021 |

(Benigni et al., 1971; List and Hörhammer, 1993)

| Hypericin content in parts per million (ppm) (Benigni et al., 1971) | |
| --- | --- |
| Flower & buds | 2150 ppm |
| Capsules | 730 ppm |
| Top leaves | 380 ppm |
| Bottom leaves | 290 ppm |
| Side stem | 120 ppm |
| Main stem | 40 ppm |
| Narrow-leaf varieties | 1040–1630 ppm (6.1 oil glands per mm) |
| Broad-leaf varieties | 370–580 ppm (2.2 oil glands per mm) |

(Benigni et al., 1971; Southwell and Campbell, 1991)

6.4.3 FLAVONOID CONTENT OF ST. JOHN'S WORT

Of 223 species of plants tested for flavonoid content, the flowers of *Hypericum perforatum* were the highest at 11.7% (Tsitsina, 1969, *Tr. Bot. Sadov. Akad. Nauk. Kaz.*, 111–114).

Among the biflavonoids, the proanthocyanidins consisting of dimers, trimers, tetramers and high polymers represent 12% of the dried weight of the aerial portion of the plant. These include the following flavonols; kaempferol, luteolin, myricetin, quercetin (2%); flavone glycosides; quercitrin (0.524–0.3%), isoquercitrin [0.3%] (Dorossiev, 1985, *Pharmazie* 585–586; Koget, 1972, *Khimiya Prirodnykh Soedinea* 242–243), hyperin [0.7–1.1% hyperoside] (List and Hörhammer, 1993), I3', II8-biapigenin [0.1–0.5%] (BergHöfer and Hölzl, 1987, *Planta Medica* 216–219; List and Hörhammer, 1993) amentoflavone, I3', II8-biapigenin (0.01–0.05% in flowers), rutin [0.3%] (Akhtardzhiev et al., 1984, *Farmatsiya* (Sophia) 34:1–6; Berghöfer and Hölzl, 1989, *Planta Medica.* 91; Kitanov, 1987, *Khimiya Prirodnykh Soedinenii* 2:185–203), gentistic acid, leucocyanidin (Benigni et al., 1971).

| Contents of tannins in *Hypericum perforatum* in g % | |
| --- | --- |
| Commercial Supplies (Whole plant) | 3–12.1 |
| Inflorescence | 12.4–16.2 |
| Leaves | 12.4 |
| Stems | 3.8 |
| Flowers *H. Perforatum* var. Vulgare | 16.2 |
| Flowers *H. perforatum* v. angustifolium | 11.1 |

(Benigni et al., 1971)

Flavonoid and procyanidin concentrations have been reported to be highest in the flowers during budding stage immediately before flowering (11.71%), followed by the leaves and stems (7.4%). Flavonoid concentrations are also reported to be highest in plants growing in higher altitudes and those growing on Northern slopes where the weight of the plant is lower than plants growing in Southern exposure (Brantner et al., 1994, *Scientia Pharmaceutica* 62:261–276; Tsitsina, 1969; Zhebeleva, 1973, *Rast. Resur.* 9:402–404). The highest concentration of I3', II8-biapigenin occurs in buds and flowers, the fruit has very low concentrations and the stems and leaves no trace (BergHöfer and Hölzl, 1987). Hyperin is highest in the flowers (3%) followed by the leaves (1.05–1.80%) and only traces in the stems [0.13%] (Maksyutina and Koget, 1971, *Khimiya Prirodnykh Soedinenii*, 3:363–367). Quercetin is found in the leaves and flowers (0.1–0.582%) with trace amounts in green leaves, higher amounts in red colored leaves, the highest amount in the leaves during flowering, and still higher amounts in the flowering tops. Rutin is found in all parts but is much higher in the leaves (2%) during the budding stage than in the flowers (0.095%), is higher in plants growing in dry vs. those growing in moist conditions, and is reported to be highest when harvested in the evening.

Sun-macerated preparations yield higher amounts of rutin than preparations macerated in the dark (Benigni et al., 1971). In one analysis of fresh material quercetin was found to be higher in the top half of the plant than in the leaves only or flowering tops only (Smith et al., 1996, Quality Validation Laboratory—Herb Pharm:Williams, Oreg., 1996).

| Flavonoid content in various parts *H. perforatum* in g % | | |
| --- | --- | --- |
| Constituent | Plant Part | Concentration |
| Total Flavonoids | flowers | 11.7 |
| Total Flavonoids | stems and leaves | 7.4 |
| Quercetin | leaves and flowers | 0.1–0.582 |
| Quercitrin | whole herb/flowers | 0.524–0.3 |
| Isoquercitrin | | 0.3 |
| Hyperin (hyperoside) | | 0.7–1.1 |
| I3, II8-biapigenin | fresh flowers | 0.1–0.5 |
| I3, II8-biapigenin | stems and leaves | non-detectable |
| I3', II8-biapigenin (amentoflavone) | flowers | 0.01–0.05 |
| Rutin | flowers | 0.095 |
| Rutin | leaves | 2 |

(Akhtardzhiev et al., 1984; Benigni et al., 1971; Berghöfer and Hölzl, 1989; Brantner et al., 1994; Dorossiev, 1985; Kitanov, 1987; Koget, 1972; List and Hörhammer, 1993; Smith et al., 1996; Tsitsina, 1969)

6.4.4 ESSENTIAL OIL FROM ST. JOHN'S WORT

The essential oil consists predominantly of monoterpenes (pinenes) and sesquiterpenes and constitutes 0.1–1% (Benigni, 1971; ESCOP, 1996). The primary compounds include the saturated hydrocarbons methyl-2-octane (16.4%) and α-pinene (10.6%); also present are traces of methyl-2-decane, methyl-2-butenol and undecane, α- and β-pinene, α terpineol, geraniol, traces of myrcene, limonene, caryophyllene, humulene, $C_{16}$ and $C_{24}$ n-alkanes, $C_{24}$, $C_{26}$ and $C_{28}$ n-alkanols (Brondz and Greibrokk, 1983, *Journal of Natural Products* 46:940–941; Brondz et al., 1983, *Phytochemistry* 22:295–296; Mathis and Ourisson, 1964, *Phytochemistry* 3:37–378).

Essential oil content in the stem is very small, and is greater in the mature capsule. It is also richer before flowering (0.26%) than when in flower (0.11%). When the stem is eliminated the plant yields an average of 0.35% essential oil (Benigni et al., 1971).

6.4.5 PHLOROGLUCINOLS IN ST. JOHN'S WORT

Phloroglucinola include hyperforin (prenylated derivative of phloroglucinol), adhyperforin (similar to the bitter principle of hops, adhumulone). Hyperforin and adhyperforin levels increase considerably during the formation of the fruits with hyperforin increasing from 2.0% in the flowers to 4.5% in the fruits based on dry weight, and polar hyperforin-like compounds increasing from 0.05–0.3%. Adhyperforin increased 10-fold from 0.2% in the flowers to 1.9% in the capsules (Benigni et al., 1971; Brondz et al., 1982, *Tetrahedron Letters* 23:1299–1300; Bystrov, 1975, *Tetrahedron Letters* 32:2791–2794; Maisenbacher and Kovar, 1992, *Planta Medica* 291–293). The hyperforins are lipophilic and unstable when exposed to heat and light.

6.4.6 MISCELLANEOUS COMPOUNDS IN ST. JOHN'S WORT

These consist of choline, carotenoids (lutein, violaxanthin, cis-throllixanthin, throllichromone), beta-sitosterol, pectin, phlobaphene and rhodan; caffeic (0.1%), chlorogenic, isovalerianic, lauric, myristic, nicotinic (0.12% in leaves), palmitic and stearic acids; amino acids including cysteine, GABA (0.7 mg/g), glutamine, leucine, lysine, ornithine, proline, threonine; scopoletin, umbelliferone; vitamin C, xanthonolignoids (1.28 mg/100 g, kielcorin) (Bennett and Lee, 1989, *Phytochemistry* 28:967–998; Karryev, 1980, *Izv. Akad. Nauk. Turkm. SSR.* 52–57; List and Hörhammer, 1993).

| Activity of Constituents | |
|---|---|
| Adhyperforin | Antibacterial (Bystrov, 1975); neurotransmitter inhibitor, potential anticarcinogenic (Oittmann et al., 1971, Arzneim-Forsch. 21:1999-2000) |
| Amentoflavone (I3', II8-biapigenin) | Anti-inflammatory, antiulcerogenic (Berghofer and Hölzl, 1989) |
| Flavonoids | Analgesic (Vasil'chenko et al., 1986) |
| Flavonols | Sedative (Berghofer and Hölzl, 1987) |
| GABA | Sedative |
| Hyperforin | Antibacterial against gram positive bacteria; wound-healing (Bystrov, 1975; Maisenbacher and Kovar, 1992) |
| Hypericin | Antiviral (Lavie et al., 1995), anxiolytic (Holly and Strowski) |
| Methyl-2-butenol | Sedative |
| Proanthocyanidins | Antioxidant, antimicrobial, antiviral, vasorelaxant |
| Xanthones | Antidepressant, antimicrobial, antiviral, diuretic, cardiotonic, $MAO_A$ inhibitor (Kitanov and Blinova, 1987) |

6.4.7 ANALYTICAL METHODS OF ANALYSIS

Two compounds of interest as marker constituents include two naturally occurring pigments, hypericin and pseudohypericin (both naphthodianthrones). These dyes are characteristic markers for this herb and are easily extracted into methanol. They both absorb visible light with a maximum absorption at 588 nm and are highly fluorescent in methanol. Both pigments are similar in their absorption and emission spectra, including their absorbtivity. Separation of these two pigments is necessary to determine the concentration of each pigment. Flavonoids are also considered to be an important class of constituents in St. John's Wort. Methods are provided for both classes of compounds.

6.4.8 THIN LAYER CHROMATOGRAPHY (TLC) OF HYPERICIN AND PSEUDOHYPERICIN

Sample Preparation

An extract of hypericin is prepared from a representative sample of dried plant material by repetitively extracting 1.0 g of the sample with four successive 10 ml portions of methanol at room temperature. The entire contents of all four extractions are diluted to 50 ml in a volumetric flask. This solution is filtered through a 0.45 µm filter prior to analysis by TLC or HPLC.

Standard Preparation

Synthetic hypericin standard (ICN Biochemical, Cleveland, Ohio, Cat #193423) is dissolved in pure methanol at a concentration of 0.10 mg/ml and filtered through a 0.45 µm filter. This standard stock solution is used for both TLC and HPLC calibration.

Stability of Standards/Sample Solutions

The literature reports that hypericin and pseudohypericin pigments, as well as solutions prepared from them are stable for months if kept in the dark. However, our data indicates they are unstable in solution.

Stop Test:

A small spot of the above extracts on filter paper will exhibit bright red fluorescence under UV-365 nm light. The liquid extract solutions are also fluoresce bright red under UV-365 nm light.

Chromatographic Conditions

The chromatographic conditions for TLC are typically as follows. Silica Gel (e.g., Eastman No. #6060-13181 with or without fluorescent indicator added to the gel) is developed with toluene:ethyl acetate:glacial acetic acid in the proportions of 3:6:1. Typically, 1–5 µl of sample is added via capillary. The detection is performed with UV light at 365 nm. Hypericin pigments also fluoresce bright red so visible light detection may be used. The Rf values for hypericin are 0.71 and for pseudohypericin 0.50. The detection limits for this assay are 0.2 µg.

6.4.9 HIGH PERFORMANCE LIQUID CHROMATOGRAPHY (HPLC) OF HYPERICIN AND PSEUDOHYPERICIN

The sample presentation and standards are prepared as described in the TLC experiment above.

The HPLC parameters are as follows. A Waters Nova-pak™ C-18 column, 3.9×150 mm is developed with a mobile phase under isocratic conditions where the mobile phase is methanol:0.4% phosphoric acid:triethylamine (82:17:1). The flow rate is 1.0 ml per minute and detection is performed using a visible detector at 588 nm. The column is run at ambient temperature. Run time is typically 12 minutes for injection of 10–50 µl of sample. The elution rates of the active components pseudohypericin and hypericin are 2.8 and 9.6 minutes, respectively.

Limits of Quantitation and Detection

Limits of detection depend upon instrumentation. When using a Waters Mod I™ HPLC system with a Waters 991M Photodiode Array (PDA) detector and monitoring at 588 nm, the detection limits are approximately 2.5 µg for both pseudohypericin and hypericin.

HPLC (Flavonoids, Hypericin and Pseudohypericin) Extraction

The residue is extracted with 40 ml acetone at room temperature for 10 minutes using an ultrasonic bath and filter. The methanol and acetone filtrates are combined and reduced to dryness under vacuum. The dry material is dissolved in 4.0 ml methanol and filtered.

The HPLC for flavonoids, hypericin and pseudohypericin is run under the following conditions.

A LichroCart™ reverse phase (RP) C-18 supersphere column, 4×250 mm with a reverse phase (RP) C-8 pre-column is developed at ambient temperature with a flow rate of 1 ml/minute for 0–39 minutes and after 40 minutes 0.6 ml per minute. The injection volume is 20 μl and detection is at 254 nm.

Three different mobile phases are used. To detect rutin, hyperoside and isoquercitrin, acetonitrile:water:phosphoric acid (16:83:1) is used with a run time of 30 minutes.

For detecting quercitrin and isoquercetin, the following system is used, acetonitrile:water:phosphoric acid (32:67:1) with a run time of 45 minutes.

For I3, II8-biapigenin, amentoflavone, pseudohypericin and hypericin the conditions are as follows. The solvent system is acetonitrile:methanol:water:phosphoric acid (55:20:24:1). The run time is 75 minutes.

The retention times (in minutes) are as follows: rutin (16.7); hyperoside (18.5); isoquercetrin (19.2); quercetin (23.8); luercetin (36.4); I3, II-biapigenin (42.8); amentoflavone (55.9); pseudohypericin (59.7); and hypericin (68.4).

Standards for rutin, hyperoside, isoquercitrin, quercitrin and hypericin are available from Sigma, St. Louis, Mo., USA, with the rest available from Roth. The samples are quantified for the procedure of Kartnig et al., 1996, *Planta Medica* 62:51–53 against an external standard in methanol at 25 μg/ml.

6.4.10 UV/VIS SPECTROSCOPIC METHOD (HYPERICIN/PSEUDOHYPERICIN)

SAMPLE PREPARATION

In one experiment a quantitative extract is prepared by extracting 1.0 g of powdered herb with three 25 ml portions of dichloromethane ($CH_2Cl_2$) or until filtrate is colorless. The dichloromethane extract is discarded. The dried residue is extracted exhaustively with acetone. The acetone extract is evaporated to dryness under vacuum. The residue is dissolved in three 8 ml portions of methanol and transferred to a 25 ml volumetric flask. Enough additional methanol is added to make the total volume 25 ml. 10 ml of this solution are filtered; the first 2 ml are discarded. 5.0 ml of the filtrate are diluted to 25 ml with methanol in a separate 25 ml volumetric flask.

6.5 HPLC ANALYSIS OF ST. JOHN'S WORT COMPONENTS HYPEROSIDE, RUTIN, QUERCETIN, QUERCITRIN, HYPERICIN, MANGIFERIN

The analytical HPLC method was as follows. The HPLC system is a Waters™ HPLC system consisting of two model 510 EF pumps, model 717 autosampler, a model 486 UV-Vis detector set at 254 nm, and a Millenium™ Version 2.15 system controller and data processing software. Separations are made using 10 μl injection volumes loaded onto a reversed-phase C-18 column (Beckman Ultrasphere™, ODS column, 5 μm, 250×4.6 mm) and a gradient elution system, using eluents A and B (A=0.1 M $NaH_2PO_4$ in 0.05% TFA $H_2O$; B=ACN) according to the following profile: 0–10 minutes 100–60% A, 0–40% B; 10–20 minutes 60–0% A; 40–100% B; 20–30 minutes 0–100% A, 100–0%B. The flow rate is kept at 1.0 ml/min., with peak monitoring at 254 nm.

Magniferin, rutin, hyperoside, quercetrin, quercetin and hypericin components are determined. The results for five commercially available samples are as follows:

| Component Name | SJ049 | SJ042 | SJ045 | SJ048 | SJ039 |
|---|---|---|---|---|---|
| Hyperoside | 5.750 | 2.660 | 4.160 | 6.310 | 24.100 |
| Rutin | 4.790 | 2.280 | 5.500 | 6.740 | 12.000 |
| Quercetin | 0.830 | 0.650 | 0.940 | 1.360 | 3.270 |
| Quercitrin | 0.910 | 0.830 | 1.050 | 1.040 | 1.560 |
| Hypericin | 0.370 | 0.140 | 0.160 | 0.110 | 0.490 |
| Mangiferin | 0.150 | 0.260 | 0.160 | 0.015 | 0.020 |
| TOTAL FOR COMPONENTS STUDIED | 12.64% | 6.22% | 11.46% | 14.32% | 41.54% |

The results are also represented in FIGS. 4 and 5. The extracts were analyzed, results are shown in FIG. 6.

HPLC Summary of Selected Products and Crude Extracts

Analysis of ABA No. SJ039, SJ042, SJ045, SJ048, SJ049, and SJ053–SJ058 with quantification of selected compounds.

The identity of these materials is as follows: Enzymatic Therapy caps (SJ039), Herb Phyters caps (SJ042), Nature's Way caps (SJ045), Jarsin 300 tabs (SJ048), Remotiv tabs (SJ049), Schaper & Brummer extract powder (SJ053), Indena extract powder lot/batch 25782/M1 and M2 (SJ054), Muggenburg extract powder (SJ055), Indena extract powder lot/batch 25917/M1 (SJ056), Plantextrakt 0.14% GmbH extract powder distributed by Botanicals International (SJ057), and Finzelberg 0.3% extract powder distributed by Botanicals International (SJ058).

The levels of mangiferin may not be reliable (NR) due to co-eluting material.

| % W/W | SJ039 | SJ042 | SJ045 | SJ048 | SJ049 | RANGE |
|---|---|---|---|---|---|---|
| mangiferin | <0.01 | 0.048 | NR | <0.01 | 0.031 | |
| rutin | 2.23 | 0.42 | 1.05 | 1.24 | 0.95 | 0.42–2.23 |
| hyperoside | 4.49 | 0.49 | 0.80 | 1.16 | 1.14 | 0.49–4.49 |
| quercitrin | 0.29 | 0.15 | 0.20 | 0.19 | 0.18 | 0.15–0.29 |
| quercetin | 0.61 | 0.12 | 0.18 | 0.25 | 0.16 | 0.12–0.61 |
| hypericin | 0.11 | 0.026 | 0.031 | 0.021 | 0.074 | 0.021–0.074 |
| Total % | 7.73 | 1.25 | 2.29 | 2.86 | 2.54 | 1.25–7.73 |
| % W/W | SJ053 | SJ054 | SJ055 | SJ056 | SJ057 | SJ058 | RANGE |

-continued

| | | | | | | | |
|---|---|---|---|---|---|---|---|
| rutin | 1.09 | 2.96 | 1.83 | 1.69 | 1.01 | 2.60 | 1.01–2.96 |
| hyperoside | 1.94 | 1.92 | 1.64 | 2.04 | 0.56 | 2.50 | 0.56–2.50 |
| quercitrin | 0.27 | 0.27 | 0.21 | 0.27 | 0.17 | 0.29 | 0.17–0.29 |
| quercetin | 1.10 | 0.53 | 0.39 | 0.63 | 0.16 | 0.32 | 0.16–1.10 |
| hypericin | 0.068 | 0.097 | 0.069 | 0.12 | 0.037 | 0.071 | 0.037–0.097 |
| Total % | 4.47 | 5.78 | 4.17 | 7.86 | 1.96 | 5.82 | 1.96–7.86 |

6.6 CONTRIBUTION OF COMPONENTS TO TOTAL ACTIVITY OF ST. JOHN'S WORT

As an illustrative example, contributions of active components to the total activity of St. John's Wort can be calculated by dividing the sum of the activities of the individual components by the activity of the total extract. The contributions of each individual component or fraction to the observed (total) bioactivity of the extract is calculated using: (i) the total bioactivity of the botanical extract in a particular assay; (ii) the amount of each component or fraction (wt/wt %) present in each extract; and (iii) the % inhibition of each purified component or fraction. This calculation is exemplified using data from Table 1A on $GABA_A$ bioactivity.

$$\Sigma f_i \times \text{spec activity/total activity} = \text{Pharmaprint \%}$$

* f=fraction weight

The total extract $GABA_A$ activity is 94% inhibition at $10^{-4}$ M. The fractions 7, 8, 9 and 10 generated from column chromatography (silica gel) have $GABA_A$ bioactivity at 40, 30, 100 and 100% inhibition at $10^{-4}$ M. The following assumptions are made: (1) the percent inhibition is linear; and (2) the average molecular weights of St. John's Wort extract and fractions is approximately the same as the active components, i.e., 200 MW.

$$100 * \left(\sum fi\cdot \text{Spec inhi/total activity}\right) = \text{Pharmaprint \%}$$

$$[(F7(0.39 \text{ g}/4.4 \text{ g})*40 + F8(0.4/4.4)*30$$

$$F9(0.7/4.4\text{g})*100 + F10(1.38 \text{ g}/4.4 \text{ g})*100)]/94 = 60.7 \%$$

The fractions 9 and 10 have maximal activity at $10^{-4}$ M, and contribute more than the above calculation indicates.

Hypericin has activity in the following assays (at $10^{-4}$ M); $GABA_A$ (130); Muscarinic MI (80); ADNS (70); Opiate NS (70); (51). However the hypericin concentration levels (0.02–0.6% w/w) are far too low (approximately two logs) to account a significant contributions to the extract activity in these assays.

The contribution of hypericin, quercetin and quercetin to the total bioactivity in the non-selective adenosine assay (AD,NS) is shown below using data from the bioactivity summary table.

$$100 * \sum Ci*\text{spec. inhi}/\text{total activity} = \text{Pharmaprint \%}$$

-continued $$100[(\text{Hypericin } Ci*70) + (\text{Quercetrin } Ci*30) + (\text{Quercetin } Ci*45)/30 =$$

$$100[(0.25*70) + (1.2*30) + (1.5*45)]/30$$

$$= 100(0.175 + 0.36 + .675)/30 = (100*1.21)/30$$

$$= 4.0 \% = \text{Pharmaprint \% based on } AD, NS \text{ Bioactivity}$$

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various publications and patents are cited in parenthesis. Their contents are hereby incorporated by reference into the present application.

We claim:

1. A method for determining a standard bioactivity for a St. John's Wort sample comprising:
   removing at least one representative first aliquot from said sample;
   measuring selective muscarinic M1 receptor binding inhibition activity of the first aliquot;
   removing at least one second representative aliquot from said sample;
   determining the concentration of hypericin in the second aliquot; and
   determining that if the bioactivity of the sample is above 30% muscarinic M1 receptor binding inhibition at a concentration of 0.0001 M, and the concentration of hypericin is at least 0.01% w/w, then the sample has a standard bioactivity.

2. A method for determining a standard bioactivity for a St. John's Wort sample comprising:
   removing at least one representative first aliquot from said sample;
   measuring selective muscarinic M1 receptor binding inhibition activity of the first aliquot;
   removing at least one second representative aliquot from said sample;
   determining the concentration of quercitin in the second aliquot; and
   determining that if the bioactivity of the sample is above 30% muscarinic M1 receptor binding inhibition at a concentration of 0.0001 M, and the concentration of quercitin is at least 0.01% w/w, then the sample has a standard bioactivity.

* * * * *